(12) United States Patent
Bell, Jr. et al.

(10) Patent No.: US 12,310,880 B2
(45) Date of Patent: *May 27, 2025

(54) DEVICES, SYSTEMS AND METHODS FOR REGULATING FLOW FROM A STOMA ON A PATIENT

(71) Applicant: OstoValve LLC, Burlington, VT (US)

(72) Inventors: Robert C. Bell, Jr., St. Johnsbury, VT (US); Damien Shulock, San Francisco, CA (US); Gary J. Margolis, Shelburne, VT (US); John Ashley, Danville, CA (US)

(73) Assignee: Ostovalve, LLC, Burlington, VT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/374,749

(22) Filed: Sep. 29, 2023

(65) Prior Publication Data

US 2024/0024151 A1    Jan. 25, 2024

Related U.S. Application Data

(60) Division of application No. 17/846,863, filed on Jun. 22, 2022, now Pat. No. 11,771,585, which is a (Continued)

(51) Int. Cl.
*A61F 5/445* (2006.01)
*A61F 5/44* (2006.01)
*A61F 5/441* (2006.01)

(52) U.S. Cl.
CPC ............ *A61F 5/445* (2013.01); *A61F 5/4407* (2013.01); *A61F 2005/4415* (2013.01); *A61F 2005/4455* (2013.01)

(58) Field of Classification Search
CPC ...... A61F 5/4405; A61F 5/4401; A61F 5/445; A61F 5/448; A61F 2005/4455
See application file for complete search history.

(56) References Cited

U.S. PATENT DOCUMENTS

| 2,586,940 A | 10/1947 | Graham |
| 4,344,434 A | 8/1982 | Robertson |

(Continued)

FOREIGN PATENT DOCUMENTS

| AU | 2009259925 B2 | 10/2015 |
| AU | 2015246069 B2 | 9/2017 |

(Continued)

*Primary Examiner* — Guy K Townsend
(74) *Attorney, Agent, or Firm* — Downs Rachlin Martin PLLC

(57) ABSTRACT

A medical appliance is configured with material that creates a fluid barrier with interior walls of a stoma on a patient. These configurations may include an annular disc with a stem on one side that inserts into the stoma. The material may reside on the stem, for example, in the form of a replaceable hollow tube that covers at least part of the stem. On the other side, a rotatable spigot inserts into a recess. The rotatable spigot has a first position that forms a flow path through the stem and the annular disc to allow waste to drain from the stoma. In one implementation, the rotatable spigot can couple with a collection device that receives the waste. The patient can return the rotatable spigot to a second position to prevent flow of waste.

15 Claims, 24 Drawing Sheets

Related U.S. Application Data continuation-in-part of application No. 16/254,453, filed on Jan. 22, 2019, now Pat. No. 12,178,738.

(60) Provisional application No. 63/270,808, filed on Oct. 22, 2021, provisional application No. 62/619,444, filed on Jan. 19, 2018.

(56) References Cited

U.S. PATENT DOCUMENTS

| | | | |
|---|---|---|---|
| 4,351,322 A * | 9/1982 | Prager | A61F 5/445 600/32 |
| 4,381,765 A * | 5/1983 | Burton | A61F 5/445 604/277 |
| 4,424,833 A * | 1/1984 | Spector | A61M 39/0606 277/560 |
| 4,634,421 A * | 1/1987 | Hegemann | A61F 2/0009 604/277 |
| 4,804,375 A * | 2/1989 | Robertson | A61F 2/0013 604/323 |
| 4,834,712 A * | 5/1989 | Quinn | A61J 15/0061 604/174 |
| 4,863,438 A * | 9/1989 | Gauderer | A61M 39/0247 604/105 |
| 6,419,699 B1 * | 7/2002 | Schuessler | F16L 27/04 604/905 |
| 6,712,800 B2 | 3/2004 | Kanbara | |
| 6,723,079 B2 | 4/2004 | Cline | |
| 6,872,189 B2 * | 3/2005 | DeLegge | A61M 39/12 604/910 |
| 6,997,909 B2 | 2/2006 | Goldberg | |
| 7,001,367 B2 | 2/2006 | Arkinstall | |
| 7,025,784 B1 * | 4/2006 | Blom | A61F 2/203 623/14.11 |
| 7,083,597 B2 * | 8/2006 | Lynch | A61M 39/02 604/174 |
| 7,087,041 B2 * | 8/2006 | von Dyck | A61F 5/445 604/338 |
| 7,172,581 B2 | 2/2007 | Ciok et al. | |
| 7,452,347 B2 * | 11/2008 | DeLegge | A61J 15/0057 604/910 |
| 7,846,144 B2 | 12/2010 | Ciok et al. | |
| 8,043,260 B2 * | 10/2011 | DeLegge | A61M 39/12 604/910 |
| 8,070,737 B2 | 12/2011 | Cline et al. | |
| 8,100,875 B2 | 1/2012 | Cline et al. | |
| 8,192,410 B2 * | 6/2012 | Smith | A61F 5/445 604/327 |
| 8,388,586 B2 | 3/2013 | Weig | |
| 8,475,356 B2 | 7/2013 | Feng et al. | |
| 8,845,606 B2 | 9/2014 | Nguyen-Demary et al. | |
| 8,900,116 B2 | 12/2014 | Hanuka et al. | |
| 8,998,862 B2 | 4/2015 | Hanuka et al. | |
| 8,998,867 B2 * | 4/2015 | Sabeti | A61F 5/4405 604/335 |
| 9,078,759 B2 | 7/2015 | Erland | |
| 9,226,848 B2 | 1/2016 | Johansson | |
| 9,498,371 B2 | 11/2016 | Salama | |
| 9,615,961 B2 | 4/2017 | Johansson et al. | |
| 9,636,249 B2 * | 5/2017 | Davies | A61F 5/445 |
| 9,943,436 B2 | 4/2018 | Nguyen-Demary et al. | |
| 10,045,877 B2 | 8/2018 | Weig | |
| 10,166,138 B2 * | 1/2019 | Cline | A61F 5/445 |
| 10,188,542 B2 | 1/2019 | Lin et al. | |
| 10,441,455 B2 * | 10/2019 | Eggert | A61F 5/4405 |
| 10,813,787 B2 | 10/2020 | Dinakara et al. | |
| 10,864,107 B2 | 12/2020 | Weig | |
| 11,033,417 B2 | 6/2021 | Bencini | |
| 11,395,757 B2 * | 7/2022 | Eggert | A61F 5/445 |
| 11,504,264 B2 | 11/2022 | Johnson et al. | |
| 11,564,827 B2 | 1/2023 | Johnson et al. | |
| 11,771,585 B2 * | 10/2023 | Bell, Jr. | A61F 5/4407 604/335 |
| 2002/0077611 A1 * | 6/2002 | von Dyck | A61F 5/442 604/332 |
| 2010/0174253 A1 * | 7/2010 | Cline | A61F 5/445 604/328 |
| 2014/0114266 A1 | 4/2014 | Arcand | |
| 2015/0164679 A1 * | 6/2015 | Maidl | A61F 5/445 604/332 |
| 2016/0287428 A1 * | 10/2016 | Eggert | A61F 5/445 |
| 2017/0367870 A1 | 12/2017 | Mariani | |
| 2018/0235802 A1 | 8/2018 | Nguyen-Demary et al. | |
| 2018/0353319 A1 * | 12/2018 | Bencini | A61F 5/4405 |
| 2018/0360643 A1 | 12/2018 | Aravalli | |
| 2019/0060105 A1 * | 2/2019 | Cesa | A61F 5/4405 |
| 2019/0201230 A1 | 7/2019 | Aravalli | |
| 2019/0224037 A1 * | 7/2019 | Bell | A61F 5/4405 |
| 2019/0380860 A1 * | 12/2019 | Eggert | A61F 5/4405 |
| 2020/0038228 A1 | 2/2020 | Aravalli et al. | |
| 2020/0038229 A1 | 2/2020 | Aravalli | |
| 2020/0155338 A1 * | 5/2020 | Meteer | A61F 5/443 |
| 2020/0397609 A1 | 12/2020 | Chang | |
| 2023/0083546 A1 | 3/2023 | Johnson et al. | |
| 2023/0218424 A1 | 7/2023 | Armstrong | |
| 2023/0320892 A1 | 10/2023 | Eyal et al. | |
| 2024/0000600 A1 | 1/2024 | Lei et al. | |

FOREIGN PATENT DOCUMENTS

| | | |
|---|---|---|
| AU | 2016225932 B2 | 11/2018 |
| CA | 2725783 C | 7/2017 |
| CA | 2772527 C | 12/2017 |
| CA | 2984082 C | 7/2019 |
| CN | 102596114 B | 10/2014 |
| CN | 106901890 B | 8/2019 |
| CN | 209220642 U | 8/2019 |
| CN | 210542011 U | 5/2020 |
| CN | 210749757 U | 6/2020 |
| CN | 117297858 | 12/2023 |
| EP | 2303201 B1 | 4/2011 |
| EP | 2150218 B1 | 7/2016 |
| EP | 3167851 A1 | 5/2017 |
| EP | 2632396 B1 | 7/2017 |
| EP | 2642958 B1 | 10/2017 |
| EP | 3284448 A1 | 2/2018 |
| EP | 3295903 A1 | 3/2018 |
| EP | 3215075 B1 | 5/2019 |
| EP | 2475340 B1 | 11/2019 |
| EP | 3785681 A1 | 3/2021 |
| ES | 2633665 T3 | 9/2017 |
| ES | 2654588 T3 | 2/2018 |
| GB | 201809053 | 7/2018 |
| GB | 2534012 B | 12/2019 |
| HR | P20171088 T1 | 10/2017 |
| JP | 5367709 B2 | 12/2013 |
| JP | 6640562 B2 | 2/2020 |
| MX | 2010013308 A | 12/2010 |
| PT | 2303201 T | 6/2009 |
| WO | 1996032904 A1 | 10/1996 |
| WO | 2011139499 A1 | 11/2011 |
| WO | 2020174497 A1 | 9/2020 |
| WO | 2020250145 A1 | 12/2020 |
| WO | 2022174288 A1 | 8/2022 |

* cited by examiner

DEVICES, SYSTEMS AND METHODS FOR REGULATING FLOW FROM A STOMA ON A PATIENT

RELATED APPLICATION DATA

This application is a divisional of U.S. Nonprovisional patent application Ser. No. 17/846,863, filed on Jun. 22, 2022, which application is a continuation-in-part of U.S. Nonprovisional patent application Ser. No. 16/254,453, filed on Jan. 22, 2019, and entitled "Regulating Flow From a Stoma on a Patient", which claims priority to U.S. Provisional Patent Application No. 62/619,444, filed Jan. 19, 2018. This application also claims priority to U.S. Provisional Patent Application No. 63/270,808, filed on Oct. 22, 2021, entitled "Devices, Systems and Methods for Regulating Flow From a Stoma on a Patient." Each of these applications is incorporated by reference herein in its entirety.

FIELD OF THE DISCLOSURE

The present disclosure generally relates to the field of osteotomy appliances. In particular, the present disclosure is directed to devices, systems and methods for regulating flow from a stoma on a patient.

BACKGROUND

Surgical procedures often require post-operative access to a patient's body cavity to drain fluids or waste that may cause infection. A "stoma" is an example of one such type of surgically created access. In one common application a stoma is an opening to allow waste from the patient's intestines to exit the body following colostomy or ileostomy surgery. The waste collects in a device, like a bag or pouch, that attaches around the stoma or connects to the stoma via a drain tube. This conventional arrangement, while effective to allow drainage, typically affords the patient little control of waste as it drains involuntarily into a collection device attached to the drain tube. Patients may elect to occlude the drain passage with, for example, a plug (in the stoma) or clamp (on the drain tube), however, discomfort may result because the stoma is not meant to tolerate occlusion for long periods of time. Damage to the drain tube may also allow waste to leak before the collection device.

SUMMARY OF THE DISCLOSURE

In one implementation, the present disclosure is directed to a stoma valve appliance, which includes an annular support member configured to surround a patient stoma and having an inner, skin facing side and an outer side; a base member removably attachable over a center of the annular support member, the base member defining a first solids and liquids flow path and a second gas vent flow path through the base member, each the flow path having at least one opening on an inner side of the base member; a valve disposed in the base member configured to control flow through the first flow path, the valve having an open position permitting flow and a closed position preventing flow and being manipulable between the open and closed position by the patient; a stem with an inlet and an outlet projecting inwardly from the body member configured to be received in the patient stoma, the stem having sufficient length to extend through the center of the annular support member to position the inlet in the stoma when the base member is mounted on the annular support member with the outlet at an opposite end communicating with the first flow path opening in the base member; and a gas permeable filter seal around the stem covering the at least one second gas vent flow path opening, whereby gasses from the stoma may be vented through the second flow path, while liquids and solids are prevented from entering the second flow path.

In another implementation, the present disclosure is directed to a patient controllable method for evacuating waste from a stoma. The method includes positioning a vented valve appliance in the stoma. the valve appliance having a closed position preventing waste from exiting the stoma and an open position allowing waste to exit the stoma; the patient selectively moving the valve appliance between the open and closed positions to evacuate waste from the stoma or retain waste within the stoma for later evacuation; and continuously venting gasses from the stoma through the valve appliance in both the open and closed positions.

In yet another implementation, the present disclosure is directed to a stoma valve appliance, which includes an annular support member configured to surround a patient stoma and having an inner, skin facing side and an outer side; a skin adhesion layer disposed on the annular support member inner, skin facing side; a base member removably attachable over a center of the annular support member, the base member defining a flow path through the base member, the flow path having an opening on an inner side of the base member; a valve disposed in the base member configured to control flow through the flow path, the valve having an open position permitting flow and a closed position preventing flow and being manipulable between the open and closed position by the patient; and an exit nozzle terminating the first path through the base member opposite the inner side opening receiving flow thought the valve in the open position.

BRIEF DESCRIPTION OF THE DRAWINGS

For the purpose of illustrating the disclosure, the drawings show aspects of one or more embodiments of the disclosure. However, it should be understood that the present disclosure is not limited to the precise arrangements and instrumentalities shown in the drawings, wherein.

Figure 1:
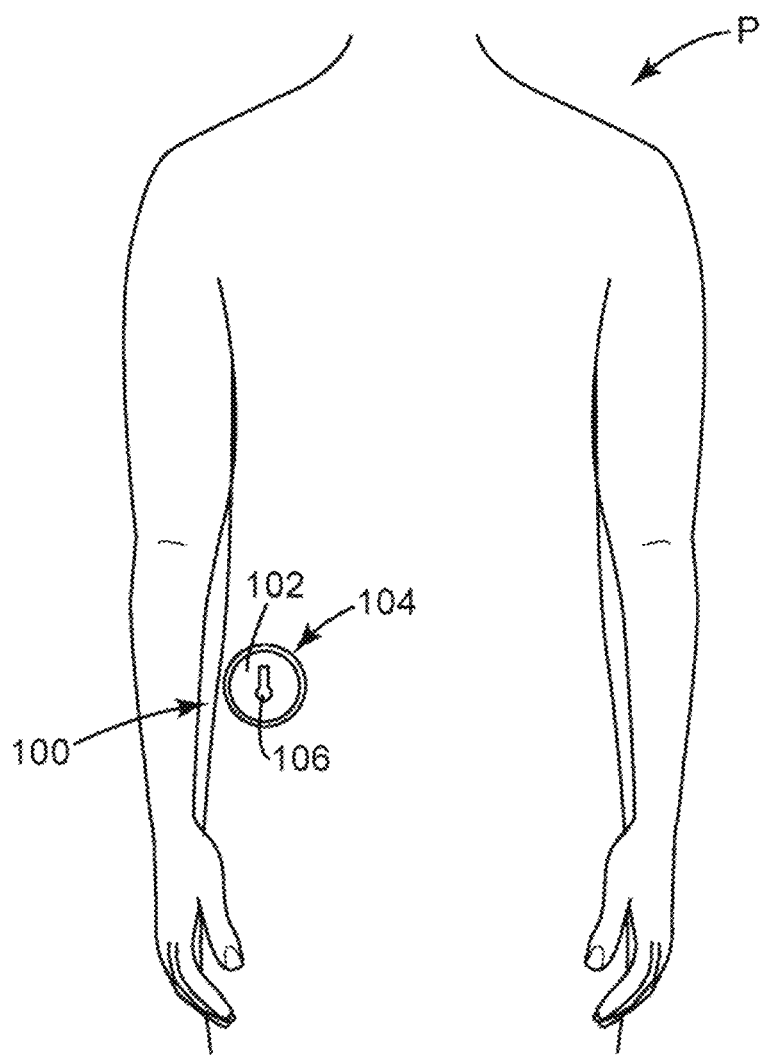
FIG. 1 depicts a sketch of an exemplary embodiment of a valve appliance in position on a patient.

Where applicable, like-reference characters designate identical or corresponding components and units throughout the several views (which are not to scale unless otherwise indicated). The embodiments disclosed herein may include elements that appear in one or more of the several views or in combinations of the several views. Methods are exemplary only and may be modified by, for example, reordering, adding, removing, and/or altering the individual stages

DETAILED DESCRIPTION

The discussion that follows describes medical appliances that can engage with surgically-formed stoma on a patient. These appliances allow patients to periodically discharge waste from their bodies into a bag or a container for proper disposal. The designs proposed allow the patient to control flow in a convenient manner while remaining properly engaged with the stoma to minimize leaks or other inadvertent discharge of waste.

FIG. 1 depicts a sketch diagram of an exemplary embodiment of a valve appliance 100. This embodiment is shown on a patient P, typically at a location on patient P where access to a body cavity is necessary after a surgical procedure. This location may have a stoma, or port, which allows waste to exit patient P into a collection device like a bag or pouch (not shown). The appliance 100 may include a support unit 102 that receives a spigot 104. A seal unit 106 may reside on part of the support unit 102 to engage with the interior of the stoma.

The support unit 102 can be configured to provide access to discharge waste from the patient's body. These configurations may embody devices with a flowpath that receives waste from the stoma. These devices may have a low-profile, preferably one that can be discretely worn under the patient's clothing.

The spigot 104 can be configured to regulate waste discharge through the flowpath. These configurations may embody devices that can move (e.g., rotate or translate) relative to the support unit 102. These devices may interface with the collection device. In use, the patient may couple the collection device to an end of the spigot 104. The patient can manipulate the spigot 104 to start flow of waste that discharges from the stoma into the collection device. When complete, the patient can manipulate the spigot 104 to cease flow, remove the collection device, and return to their daily activities.

The seal unit 106 can be configured to seal the support unit 102 to the stoma. These configurations may embody devices made of materials that "self-seal" to create a fluid-tight or fluid-proof barrier between surfaces on both the device and the stoma. Preferably, the material does not require interaction with the patient to create this barrier. Exemplary materials may expand (in size or volume) inside of the stoma, for example, in response to contact with fluid (or other hydraulic interactions). The material may also absorb fluids to prevent migration of waste out of the patient's body. These features significantly simplify use and maintenance because the patient can rapidly remove and replace the material as part of their regular care or maintenance of the appliance 100.

Figure 2:
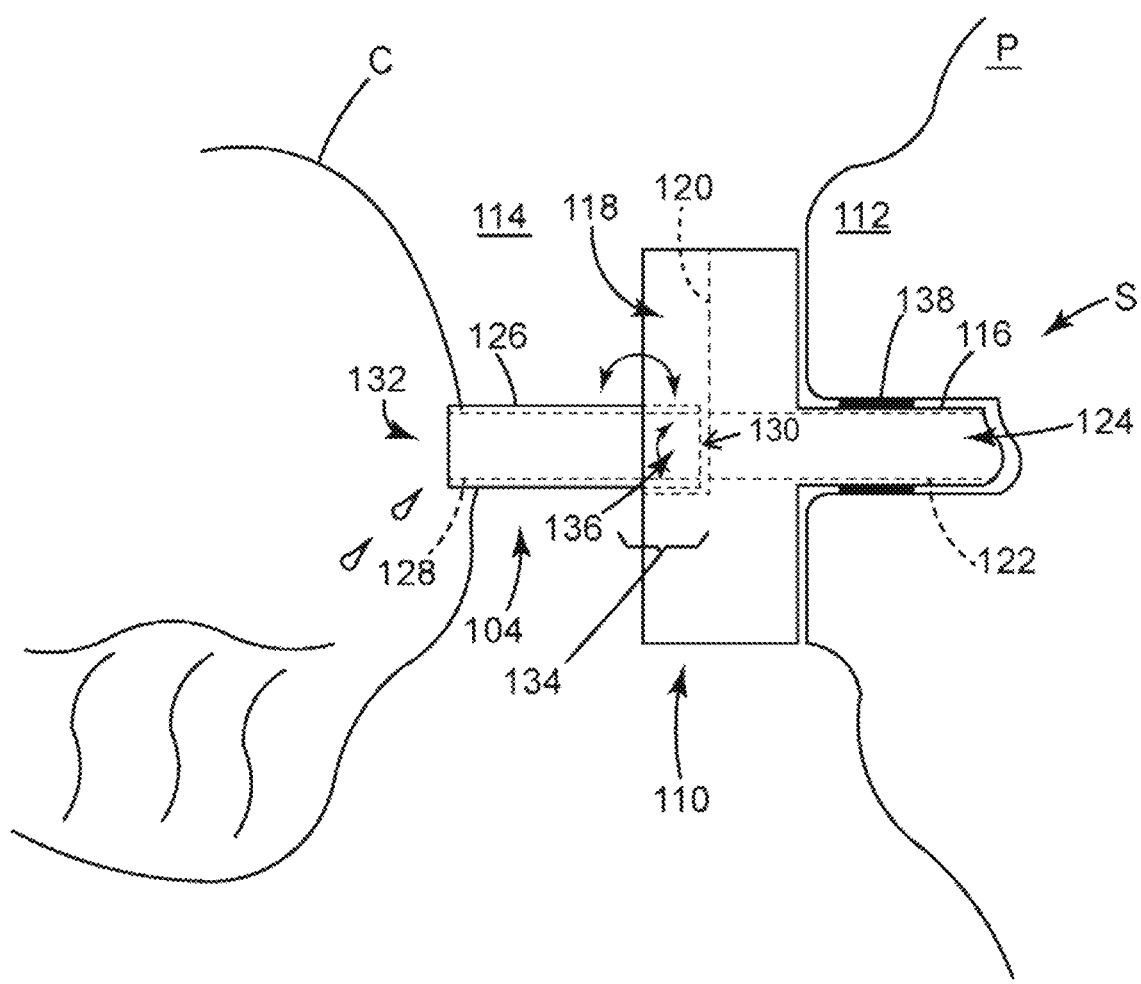
FIG. 2 depicts an elevation, side view of the valve appliance of FIG. 1.

FIG. 2 depicts a schematic diagram of an elevation view from the side of an example of the valve appliance 100 of FIG. 1. The support unit 102 may include a body 110 with a proximal side 112 and a distal side 114. The proximal side 112 may contact patient P with the appliance 100 in position at the stoma, shown and identified generally by the letter S. A stem 116 may extend from the proximal side 112. The stem 116 may form a cylinder that inserts into the stoma. The cylinder may form integrally with the body 110 as a single or monolithic piece. On the distal side 114, the body 110 may have a recess 118 that forms a back surface 120. A through-bore 122 may extend from the back surface 120 through the body 110 and the stem 116. The through-bore 122 creates a drain passage 124 for waste to exit patient P through stoma S.

Figure 3:
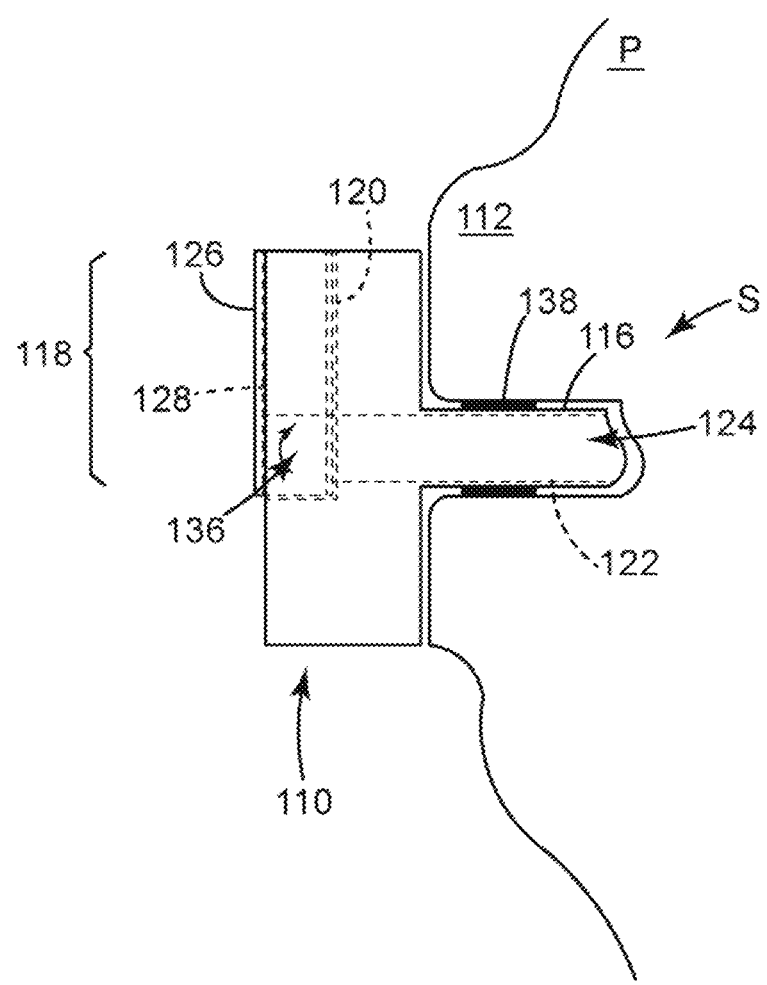
FIG. 3 depicts the side view of the valve appliance of FIG. 1, with the valve appliance in a different configuration.

The spigot 104 may be configured to fit into the recess 118. These configurations may comprise an elongated body 126, itself with a through-bore 128 that creates open ends (e.g., a first open end 130 and a second open end 132). The first open end 130 may insert into the cut-out recess 118, creating an articulating joint 134 with at least one degree of freedom (identified here as rotation about an axis 136). The axis 136 may extend perpendicular to the drain passage 124. A snug interference fit may be useful at the articulating joint 134 to retain the elongate body 126 in the recess 118, but not frustrate rotation about the axis 136. In use, the articulating joint 134 allows the elongated body 126 to change orientation relative to the body 110 to regulate flow of waste from stoma S. A first orientation for the elongated body 126 may align the through-bore 128 with the drain passage 124, as shown in FIG. 2. This orientation "opens" the appliance 100 to permit waste to flow into, for example, the collection device C that couples with the second open end 132 of the elongate body 126. As best shown in FIG. 3, rotation of the elongate body 126 to a second orientation causes misalignment of the through-bore 128 and the drain passage 124. This orientation "closes" the appliance 100 to block flow of waste out of stoma S. In this orientation, the elongate body 126 may fit into the recess 118 for it to stow out of the way when not "open" for use with collection bag C.

The seal unit 106 may be configured to fit onto the cylinder of the stem 116. These configurations may include a sleeve 138, for example, a hollow tube that can fit between the outer surface of the stem 116 and the inner wall of stoma S. The hollow tube may cover all or part of the stem 116. Suitable materials may include cotton, rayon, or other "tampon-like" materials that can absorb moisture or expand in size or shape. These materials may be suitable along or in combination with other materials (e.g., synthetic fibers like viscose rayon). In one implementation, the tube of material may form an annular seal with the inner wall of the stoma. This annular seal may secure or hold the appliance 100 in place (possibly to foreclose the need for a belt). It may also prevent leaks of waste from patient P, for example, from around the periphery of the stem 116. In one implementation, the sleeve 138 can be configured to allow an end user to remove a first sleeve 138 of material from the stem 116 in favor of a second sleeve 138 of material. This second sleeve 138 of material may correspond with new material that replaces the soiled first sleeve 138 of material. This feature allows the end user to clean and sterilize the appliance 100, as well as to maintain integrity (and cleanliness) of the sleeve 138 to avoid potential infection or other issues that may arise due to prolonged exposure of the sleeve 138 inside of stoma S.

Figure 4:
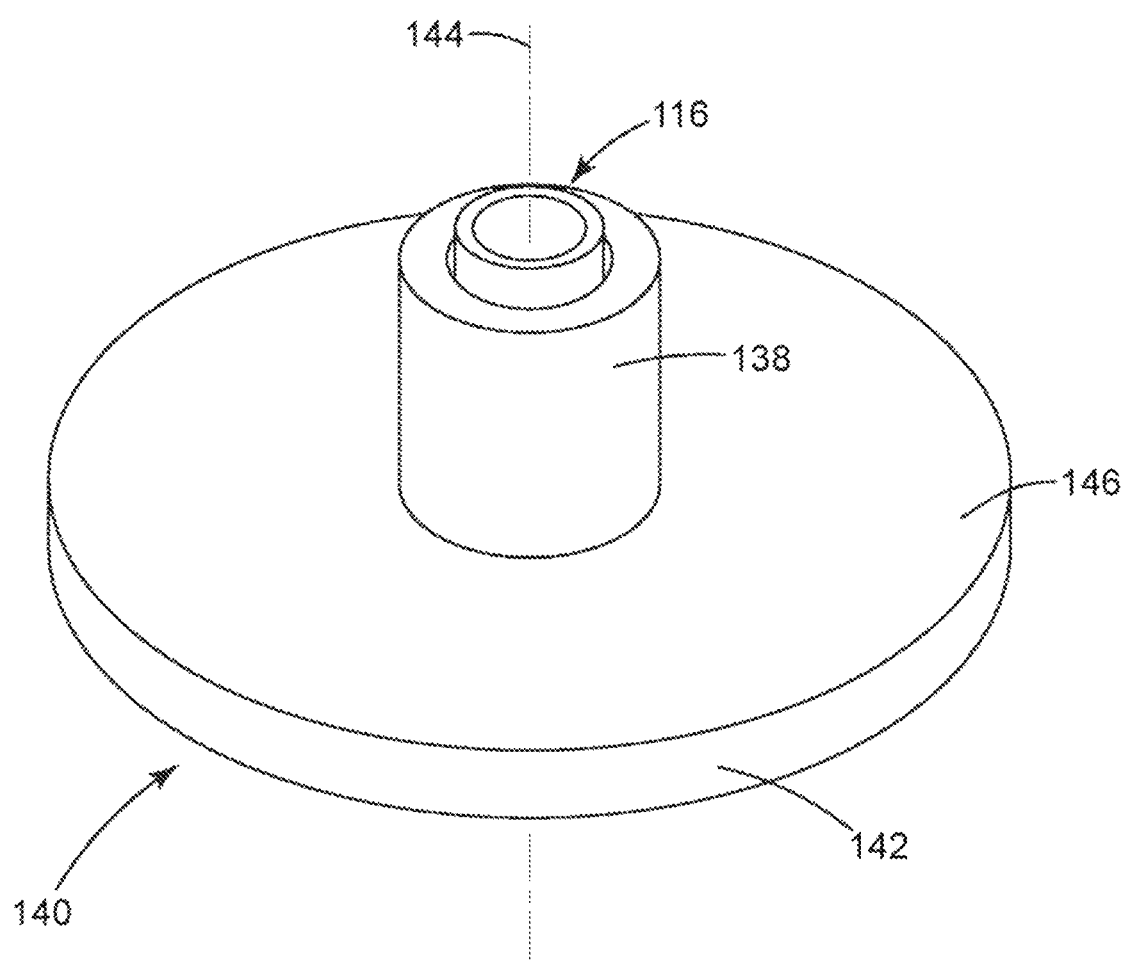
FIG. 4 depicts a perspective view from the top of an example of the valve appliance of FIG. 1.

FIG. 4 depicts a perspective view of exemplary structure for the body 110 for use in the valve appliance 100 of FIG. 1. This structure includes a disc portion 140 with an outer peripheral surface 142 that circumscribes an axis 144. The outer peripheral surface 142 may have an annular or circular shape, although other shapes, like a square, may also suffice.

On the proximal side 112, the disc portion 140 may form a flat, planar surface 146, which as noted above may rest against patient P.

Figure 5:
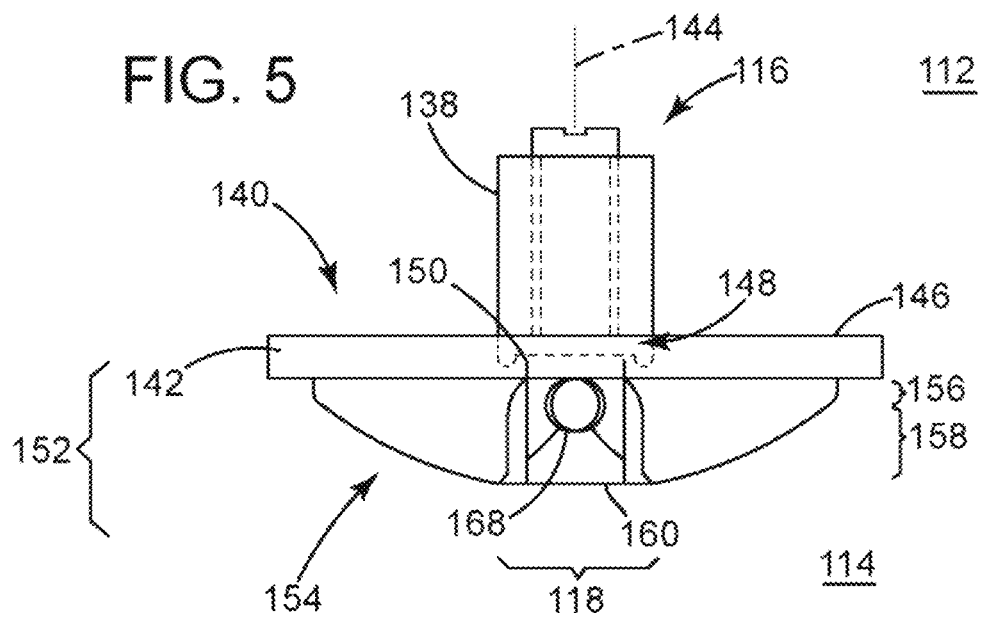
FIG. 5 depicts an elevation view from the side of the example of FIG. 4.

FIG. 5 shows an elevation view from the side of the example of FIG. 4. The planar surface 146 may include a shallow recess 148, for example, a circular cut-out or groove that aligns with (or circumscribes) the axis 144 and terminates at a bottom 150. Dimensions for the recess 148 may permit at least part of the sleeve 138 to set into the material of the disc portion 140. On the distal side 114, the body 110 may have a boss member 152 that resides on the disc portion 140, opposite the stem 116. The boss member 152 may have an outer surface 154 with a first portion 156 that is perpendicular or near-perpendicular with the axis 144. The first portion 156 terminates at a second portion 158, which has a generally domed or bulbous profile. This profile may flatten at top 160.

Figure 6:
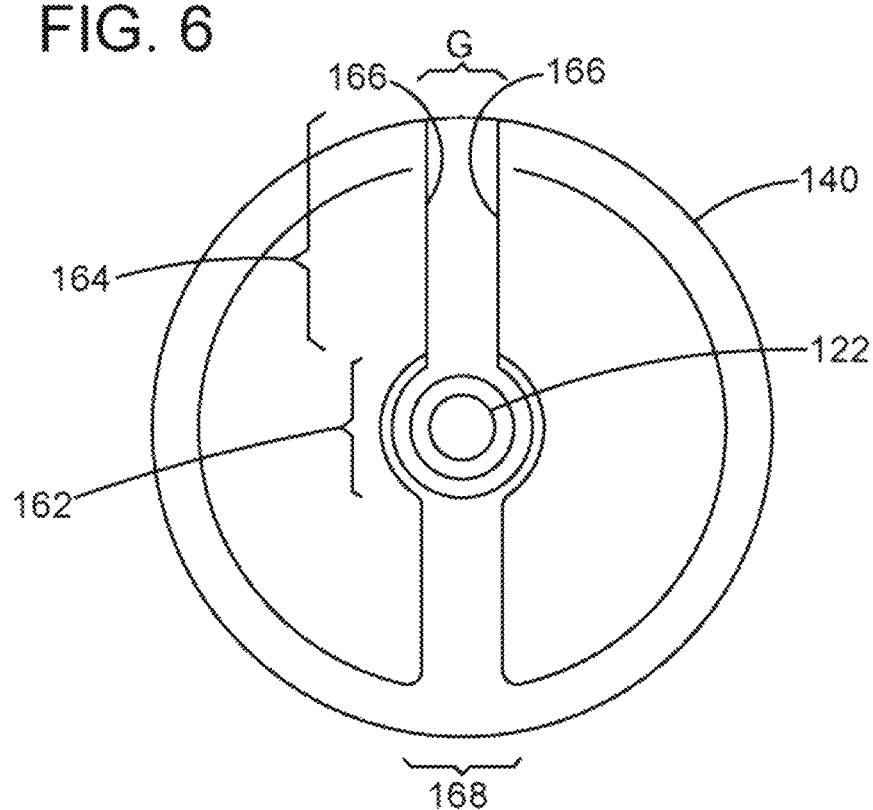
FIG. 6 depicts a plan view from the top of the example of FIG. 4.

With reference also to FIG. 6, which is a plan view of the distal side 114 of the body 110, the recess 118 may have a first portion 162 that exposes the drain passage 124. Geometry for the first portion 162 may match corresponding geometry of the elongated body 126 of the spigot 104. The recess 118 may also have a second portion 164 that may extend radially outwardly from the first portion 162 to the perpendicular portion 156 of the outer surface 154. The second portion 164 may form opposite side walls 166 that are spaced apart from one another by a gap G. Examples of gap G are large enough to receive the elongated body 126 of the spigot 104. In one implementation, the body 110 may include an aperture 168 that extends in a direction opposite of the recess 118.

Figure 7:
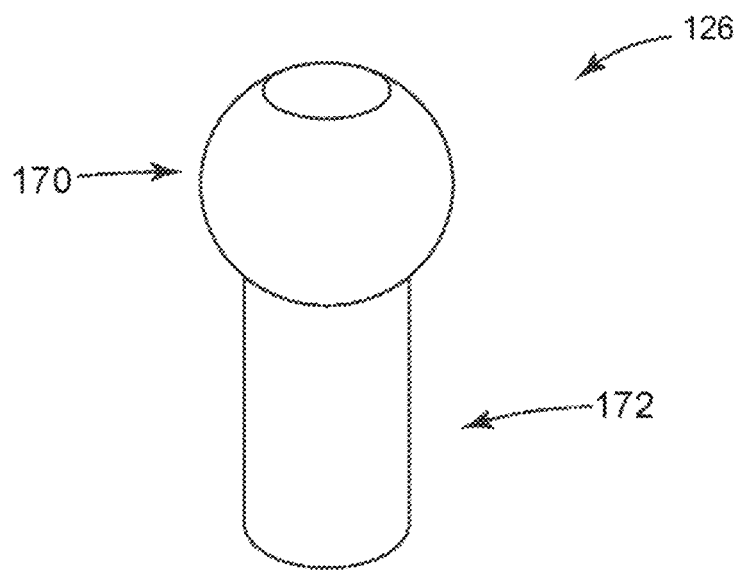
FIG. 7 depicts a perspective view of an example of a spigot for use in the example of FIG. 4.

FIG. 7 depicts a perspective view of an example of the elongated body 126 of the spigot 104. This example may have a bulbous, rounded portion 170 and a cylindrical portion 172. The rounded portion 170 may insert into the first portion 162 of the recess 118. As noted above, the fit may be snug, with appropriate tolerance interference to hold the elongated body 126 in position but still allow it to change orientation relative to the boss member 152.

Figure 8:
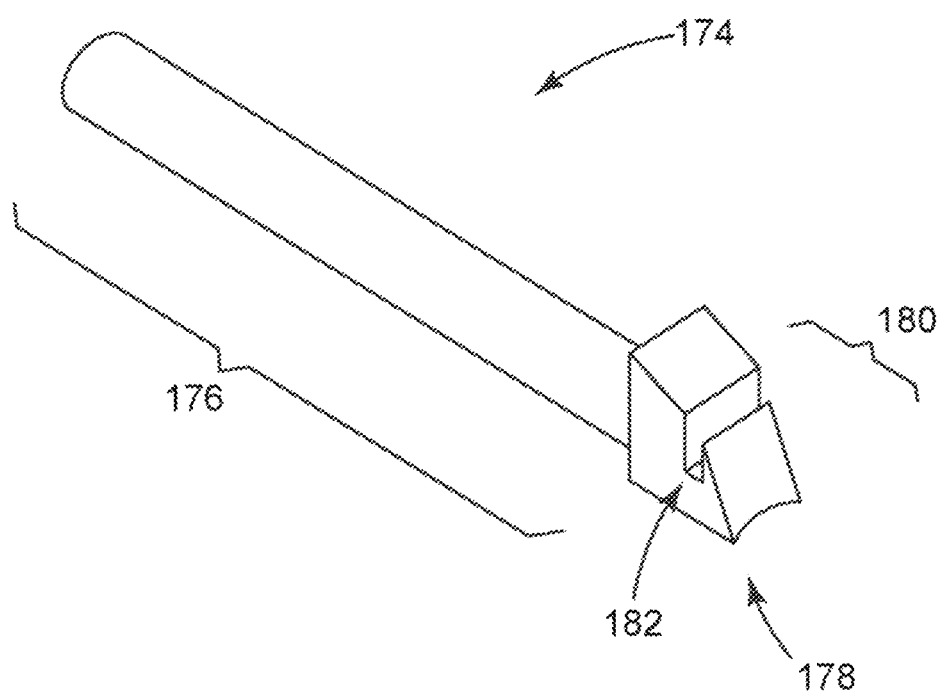
FIG. 8 depicts a perspective view of an example of a tool for use with the example of FIG. 4.

FIG. 8 depicts a perspective view of an example of a tool 174 for use with the appliance 100. The tool 174 may have an elongated, cylindrical body 176 that terminates at a locking feature 178. As shown, the locking feature 178 may form a chamfered head 180 that incorporates a slot 182. In use, the tool 174 may slide into the second open end 132 of the elongated body 126 and extend out the first open end 130. 126. In this configuration the tool may prevent rotation of the spigot 104. In one example, the slot 182 may concomitantly engage with features on the body 110 to prevent the tool 174 from "backing out" of the aperture 168. Pressing on the chamfered head 180 can disengage the slot 182 and allow an end user to withdraw the tool 174. This feature frees the spigot 104 to move to its "open" orientation to allow waste to exit stoma S. The end user may also utilize the tool 174 to clean out the drain passage 124 to remove any waste that could block flow from stoma S.

Figure 9:
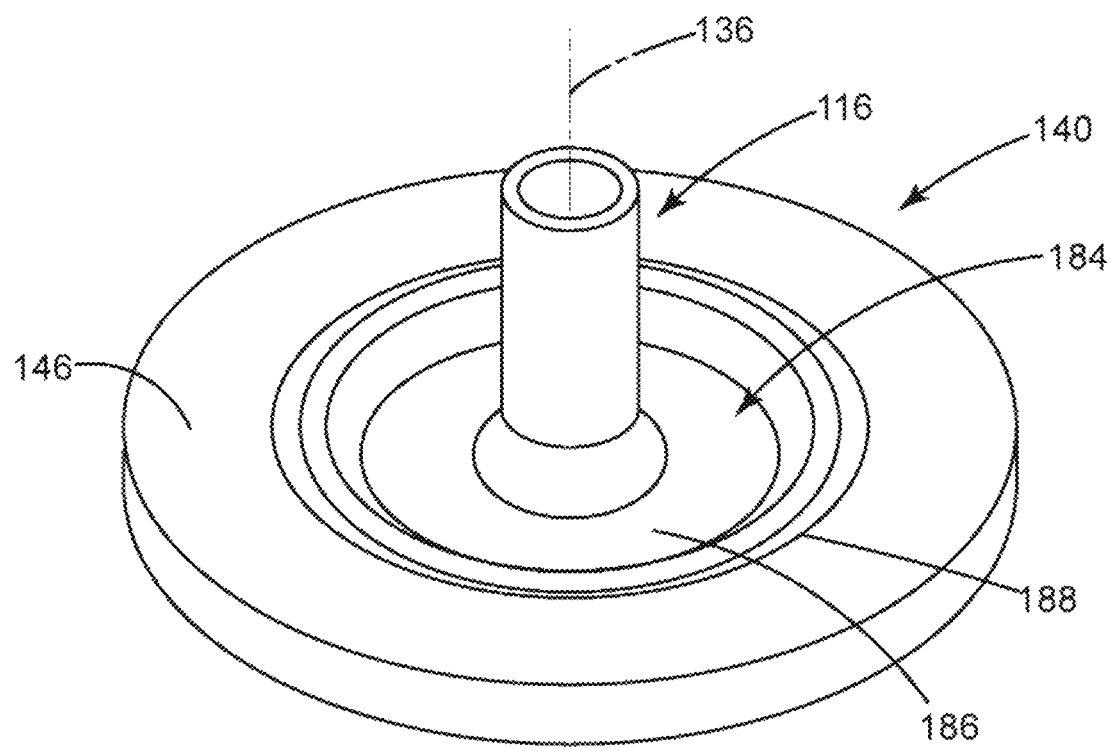
FIG. 9 depicts a perspective view of another example of the valve appliance of FIG. 1.
Figure 10:
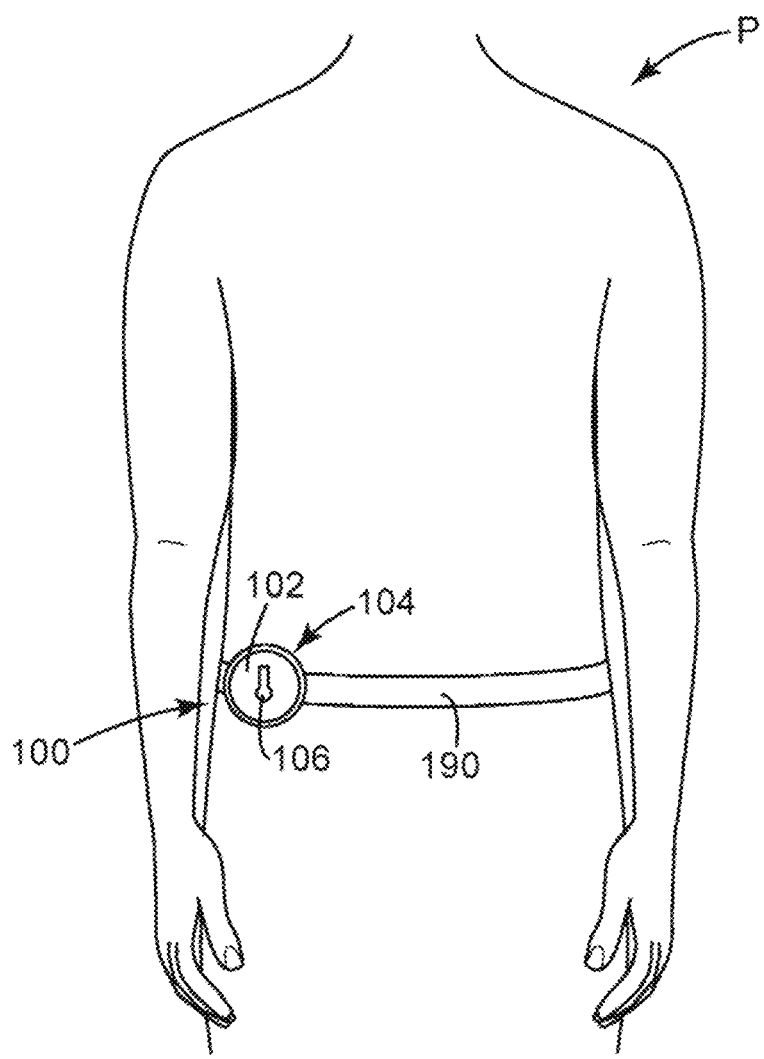
FIG. 10 depicts a sketch of the example of FIG. 9 on a patient.

FIG. 9 depicts a perspective view of another structure for the body 110 for use in the valve appliance 100 of FIG. 1. The planar surface 146 may include a central bore 184 that penetrates into the material to form a bottom 186. An annular groove 188 may circumscribe the bore 184. In one implementation, the seal unit 106 may include an O-ring or gasket that fits into the annular groove 188. A thin membrane made of compliant, flexible material may be useful to interpose between the planar surface 146 and patient P. These materials can prevent irritation of the skin of patient P under direct contact from the body 110 for long periods of time. As best shown in FIG. 10, a belt 190 may be required to secure the appliance 100 in place to allow patient P to carry on with daily functions.

Figure 11A:
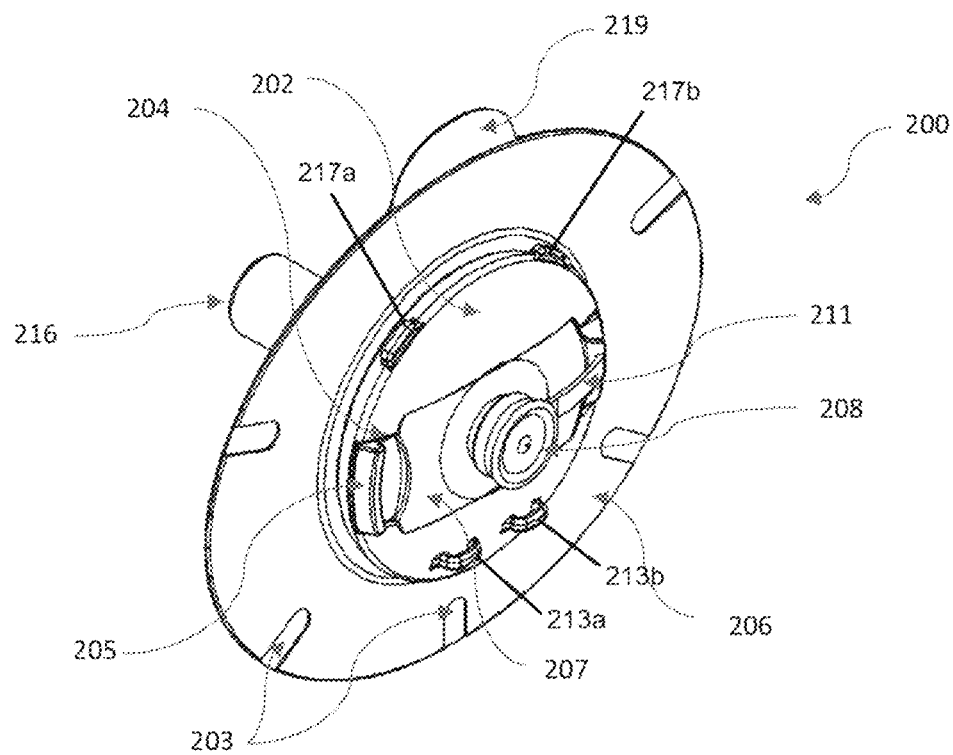
FIG. 11A is a perspective view of an embodiment of a valve appliance.
Figure 11B:
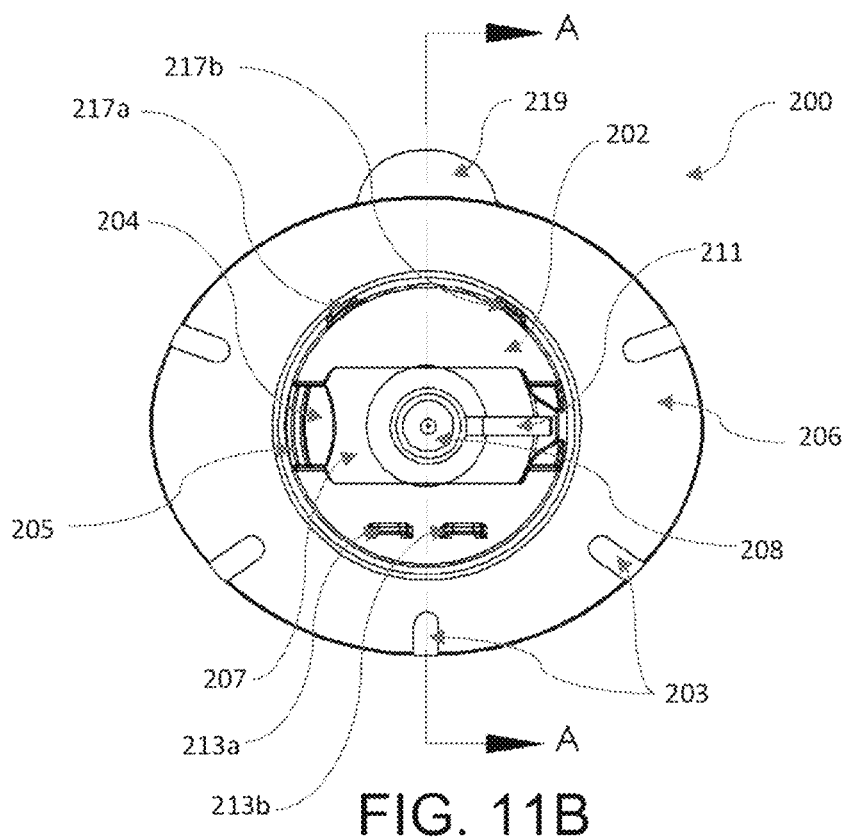
FIG. 11B is a front view of the embodiment of the valve appliance shown in FIG. 11A.

FIGS. 11A and 11B depict a further alternative embodiment of a valve appliance 200 configured to interface with a patient's stoma to allow patient-controlled elimination of waste through the stoma. The valve appliance 200 is comprised of a base 202 that is attached to an adhesive wafer 206, which may be formed as a relatively thin, flexible annular disk. The adhesive wafer 206 is configured with adhesive on the back side 212 for securing the valve appliance 200 to a patient's skin. For example, an adhesive surface 258 (FIG. 12B) on the adhesive wafer 206 bonds the adhesive wafer 206 to the skin. Adhesive surface 258 can be comprised of any type of skin compatible adhesive such as a colloidal hydrogel adhesive. The adhesive wafer 206 can also include a removal tab 219 used to assist the patient when they want to remove the adhesive backed wafer from their skin and flex joints 203 that allow the adhesive wafer 206 to closely conform to the irregular contours of the patient's skin. The base 202 has one or more bag clip engagement slots 213a and 213b and one or more bag clip engagement tabs 217a and 217b. The bag clip engagement slots 213a and 213b and bag clip engagement tabs 217a and 217b are configured to hold a bag clip as will be described later herein. The base 202 engages a gate valve 204 that sits on the front of the base 202. The gate valve 204 has a valve handle 205 on one end to enable the patient to open and close the gate valve 204 as will be described later herein. The gate valve 204 is constrained to the base 202 by a valve cover 207. The valve cover 207 and base 202 constrain the gate valve 204 but allow the gate valve 204 to slide open and closed as will be described further herein. The valve cover 207 includes an exit nozzle 226 that guides effluent away from the valve appliance 200. The exit nozzle 226 can be covered by a nozzle cap 208 when the patient is not operating the valve appliance 200 to remove effluent. The nozzle cap 208 is connected to the base portion 202 by means of a tether 211. The tether 211 keeps the nozzle cap 208 connected to the valve appliance 200 when the patient removes the nozzle cap 208 from the exit nozzle 226.

Figure 11C:
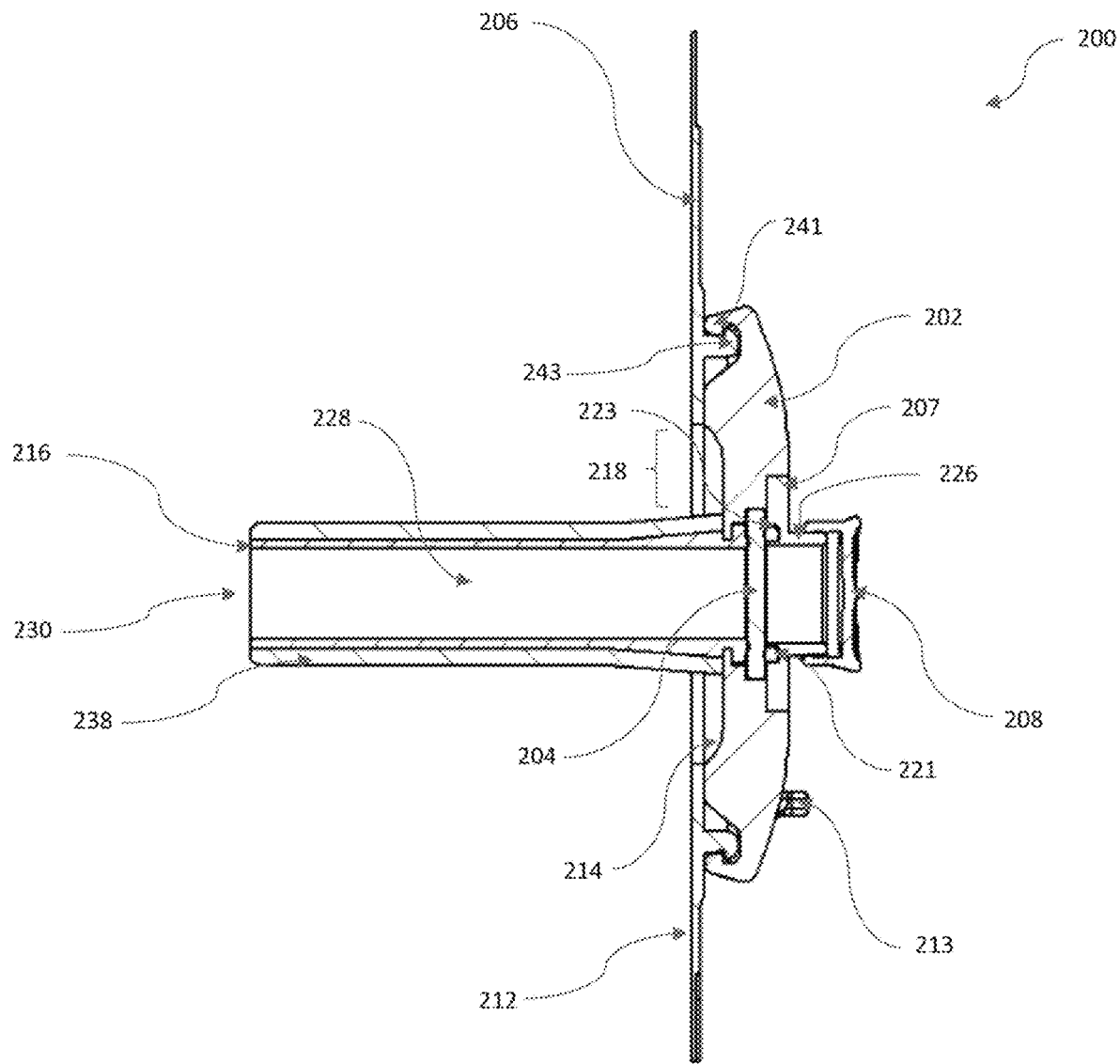
FIG. 11C is a cross-sectional view of the embodiment of the valve appliance shown in FIG. 11B through line A-A.

FIG. 11C depicts how the base portion 202 is engaged with the adhesive wafer 206 by a base clip 241 that engages with a wafer clip 243. Using a base clip 241 on the base portion 202 and wafer clip 243 on the adhesive wafer 206 allows the two parts to be connected and to separate as needed. For example, the patient might want to attach the base 202 to a smaller diameter adhesive wafer 206 that conforms better to their skin than the standard diameter adhesive wafer 206. Likewise, the patient might want to attach the base portion 202 to an adhesive wafer 206 that has a different type of adhesive that is more compatible with the patient's skin. Compatibility of the adhesive to the patient's skin is a very important characteristic of the valve appliance 200 as the patient will keep the valve appliance 200 attached to their skin for 2 or more days before removing the valve appliance 200 to replace it with a new one. The adhesive wafer 206 is also comprised of an annual opening 218, and the base 202 is comprised of a domed cavity 214. The annular opening 218 and domed cavity 214 are configured to cover the patient's stoma that often protrudes from the surface of the patient's skin without compressing or otherwise impacting the stoma. It is important to accommodate the stoma without irritating it by providing a cavity comprised of the annular opening 218 and domed cavity 214. The patient's stoma can change size and shape over time so allowing the patient to interchange the adhesive wafer 206 for different sizes and/or adhesive types. Alternatively, in some embodiments, adhesive wafer 206 may be configured to allow the patient to trim the annular opening to accommodate the patient's particular stoma size and shape. Similarly, the base 202 may be exchanged with other bases to provide a domed cavity 214 to best match the stoma shape and size. The two-piece configuration disclosed herein thus provides further advantages in patient comfort based on the patient having the ability to control and change shapes and adhesion types over time without needing to replace the entire device.

Figure 22A:
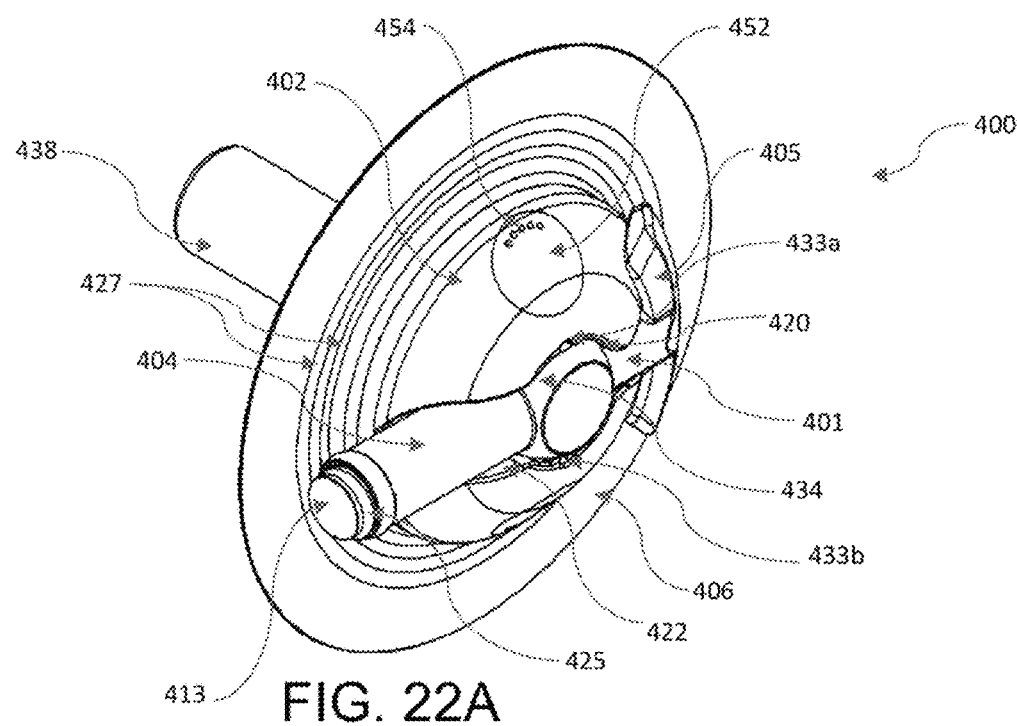
FIG. 22A is a perspective view of yet another embodiment of a valve appliance.
Figure 22B:
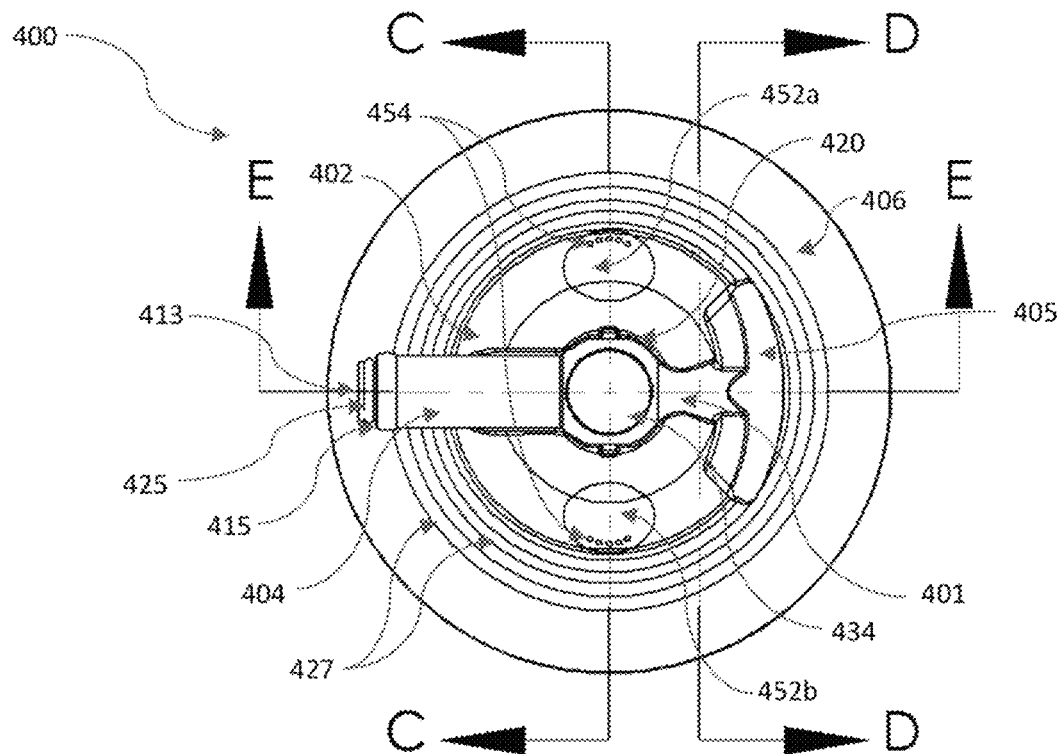
FIG. 22B is a front view of the embodiment of the valve appliance shown in FIG. 22A.
Figure 22C:
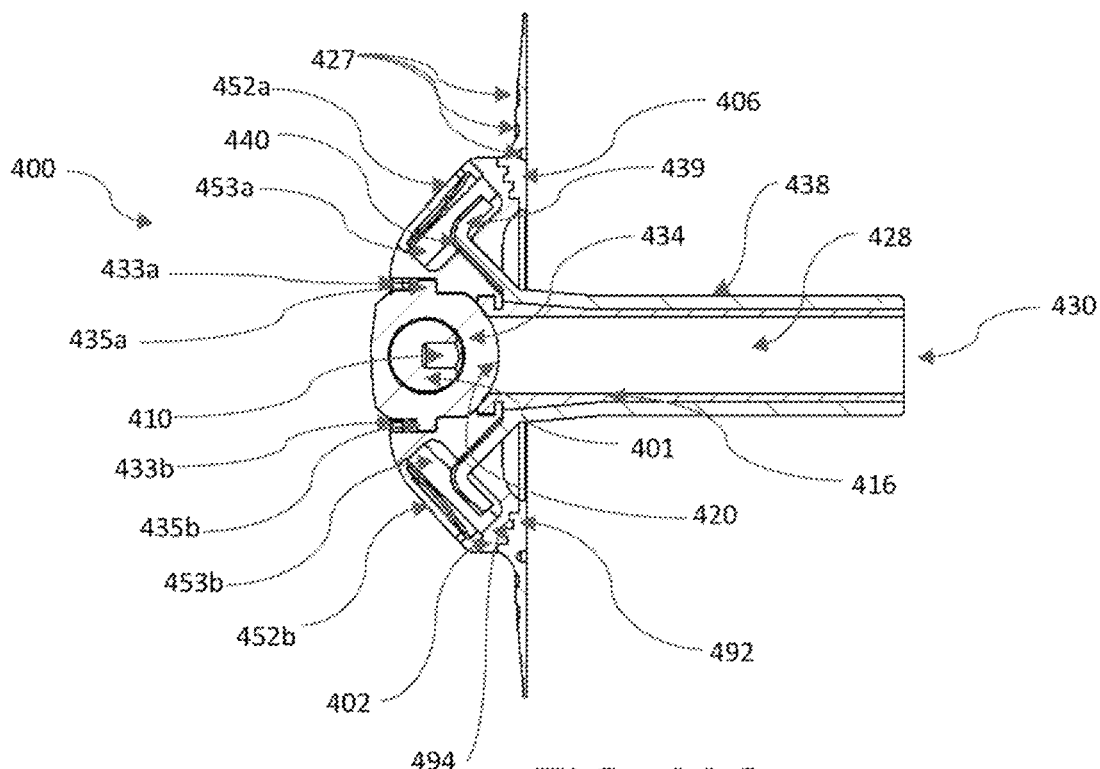
FIG. 22C is a cross-sectional view of the embodiment of the valve appliance shown in FIG. 22B through line C-C.
Figure 22D:
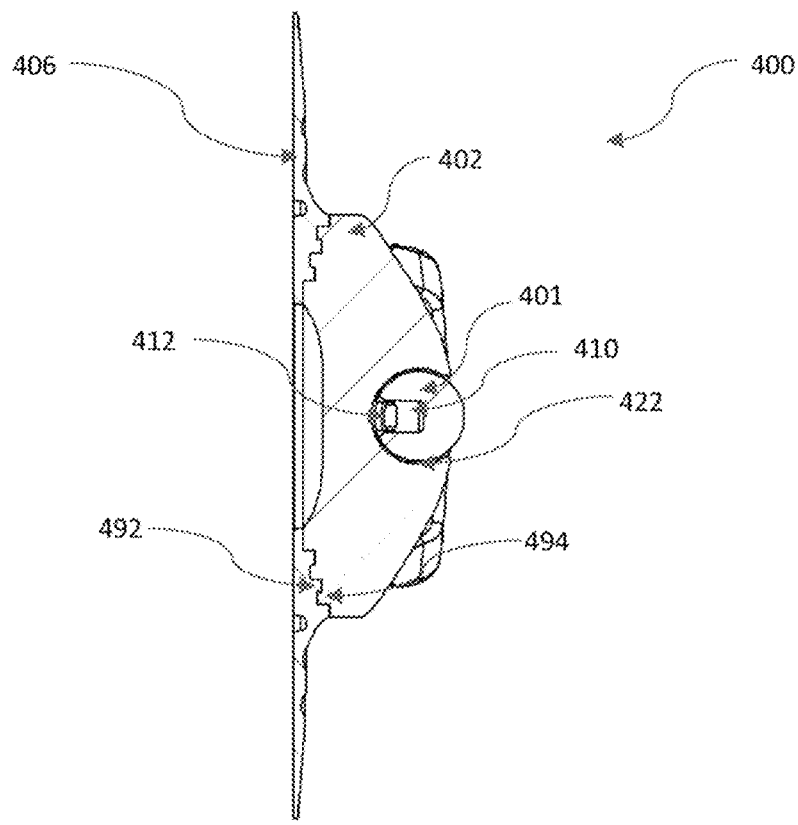
FIG. 22D is a cross-sectional view of the embodiment of the valve appliance shown in FIG. 22B through line D-D.
Figure 22E:
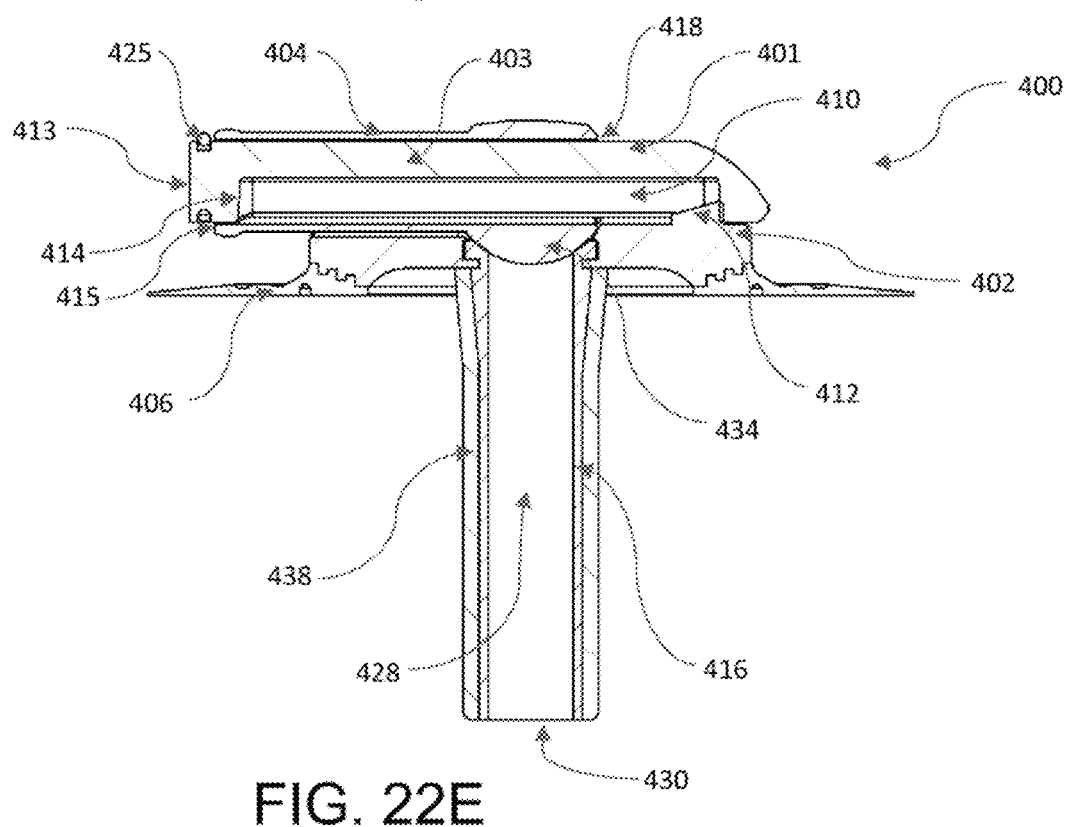
FIG. 22E is a cross-sectional view of the embodiment of the valve appliance shown in FIG. 22B through line E-E.

The base clip 241 and wafer clip 243 are not the only possible configuration for removably connecting the base 202 and adhesive wafer 206. In one alternative, the base clip 241 and wafer clip 243 could be replaced with interlocking threads allowing the base 202 and adhesive wafer 206 to be screwed together and screwed apart. If threads are used rather than the base clip 241 and wafer clip 243 then a detent, latch, compression washer, or other restraining device may be required in addition to the threads to prevent the threads from separating unless intended. An arrangement of interlocking ribs and grooves, such as shown in FIG. 22D and described below, also may be used. Other removeable connectors such as hook and loop fastening devices and other snap or interference fit devices also may be employed.

The valve cover 207 is configured with an annular recess 223 that is configured to hold an annular seal 221. The annular seal 221 is compressed against the valve cover 207 and the valve gate 204 to ensure that no effluent leaks between the valve cover 207 and the valve gate 204. The annular seal 221 could be an O-ring type seal. The annular seal 221 could also be any other type of seal as are commonly used to prevent fluid leakage between two parts. The annular seal 221 could also be adhesively or otherwise bonded to the valve cover 207 rather than compressed against the valve cover 207. The annular seal 221 could also be molded onto the valve cover 207.

On the back side of the valve appliance 200 there is a stem 216 that is covered by a gas permeable filter 238. The back end of the stem 216 has an entry port 230 that allows effluent to enter the drain passage 228. As shown in FIG. 11C, the valve 204 is in the closed position and as such is blocking the drain passage 228 and preventing effluent that enter the drain passage 228 from exiting the patient's stoma. The gas permeable filter 238 is configured to be compressed against the inside diameter of the stoma and prevent effluent from leaking between the outer surface of the gas permeable filter 238 and the stoma.

Figure 12A:
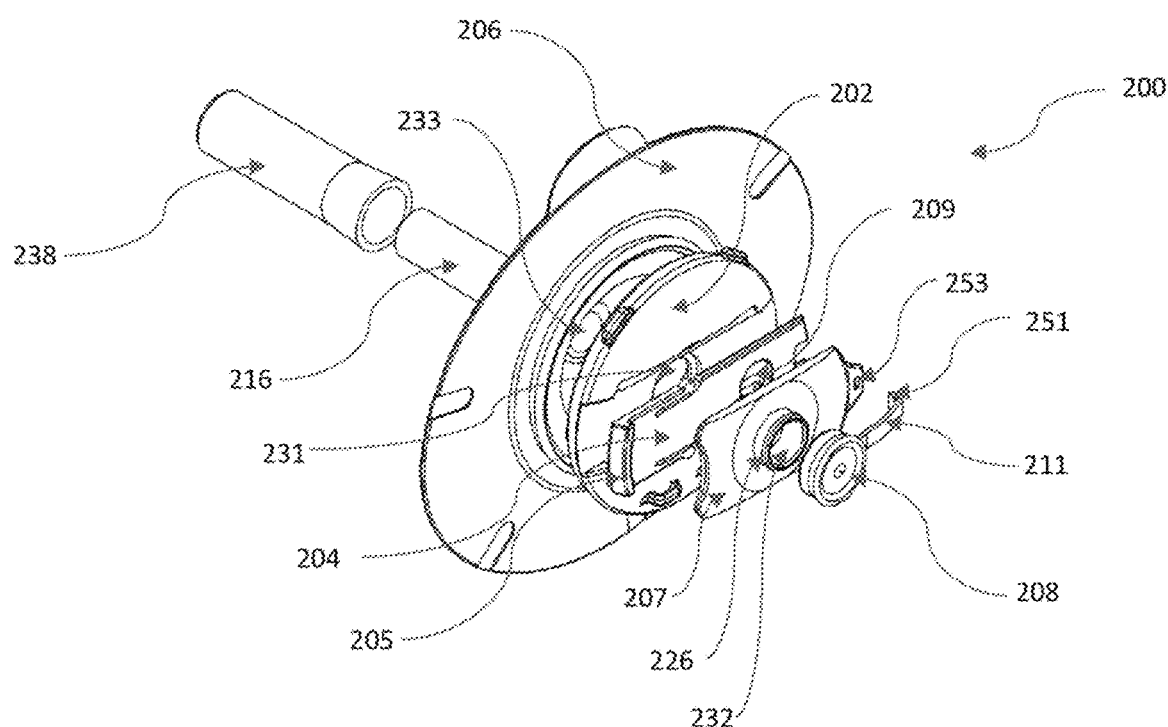
FIG. 12A is an exploded perspective view of the embodiment of the valve appliance shown in FIG. 11A.
Figure 12B:
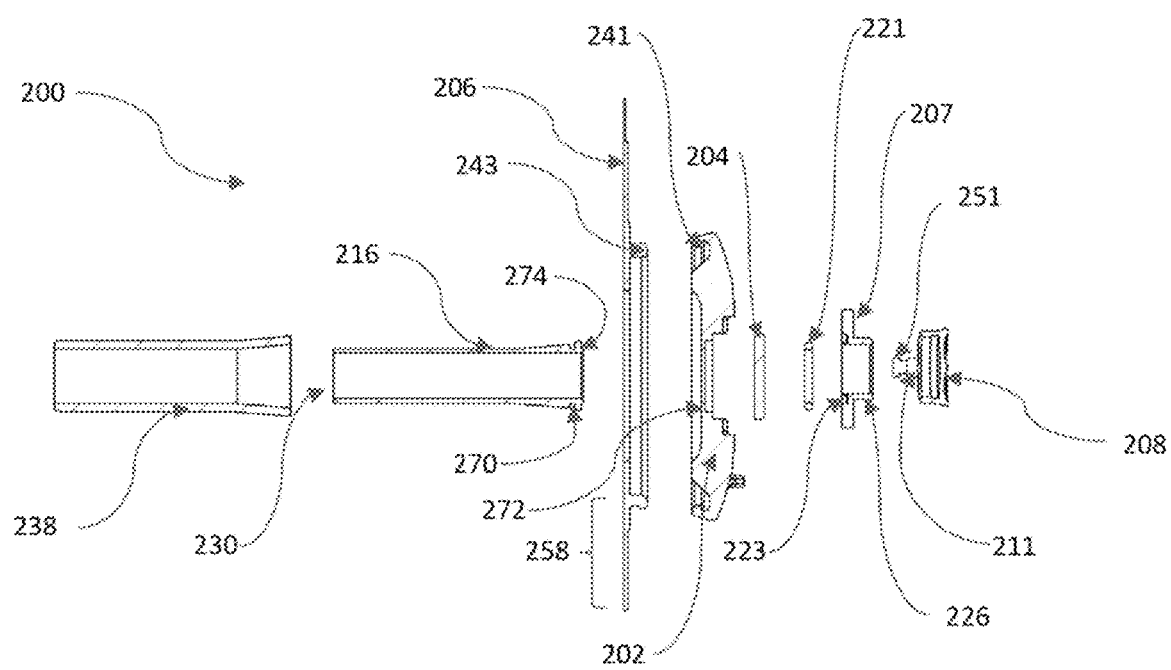
FIG. 12B is an exploded cross-sectional view of the embodiment of the valve appliance shown in FIG. 12A through line A-A (as shown in FIG. 11B).

The front of the stem 216 is comprised of a slot 270 and a protrusion 274 as depicted in FIG. 12B. The slot 270 is configured to interface with a ledge 272 on the base 202 and thereby connect the stem 216 to the base 202. This connection between the slot 270 and the ledge 272 can be a simple overlapping connection. The connection can also include adhesive or similar bonding between the slot 270 and the ledge 272. The stem 216 could also be molded onto the base 202. The protrusion 274 is configured to seal against the backside of the gate valve 204 to prevent effluent in the drain passage 228 from leaking around the gate valve 204.

Referring to FIG. 12A, the valve cover 207 is shown with a tether slot 253 configured to receive and constrain a tether tab 251 on the end of the tether 211 opposite the nozzle cap 208. Although the tether slot 253 is shown as part of the valve cover 207 it could also be configured to be part of the base 202. A tether slot 253 and tether tab 251 are just one possible method for constraining the nozzle cap 208 and tether 211 to the rest of the valve appliance 200. The tether 211 could be adhesively or otherwise bonded to the valve cover 207 or to the base 202. The tether 211 could also be molded to the valve cover 207 or to the base 202.

The base 202 is shown with a base opening 231 that is aligned with the drain passage 228. The base opening 231 is also aligned with a valve cover opening 232 at the front end of the exit nozzle 226 on the valve cover 207. The gate valve 204 also has a gate opening 209. The entry port 230, drain passage 228, base opening 231 and valve cover opening 232 are all aligned to allow effluent to exit through the valve appliance 100. However, in the configuration depicted in FIGS. 11A-C and 12A-B, the gate opening 209 is not aligned with the entry port 230, drain passage 228, base opening 231 and valve cover opening 232 and the valve appliance 200 is closed by the gate valve 204.

Figure 13A:
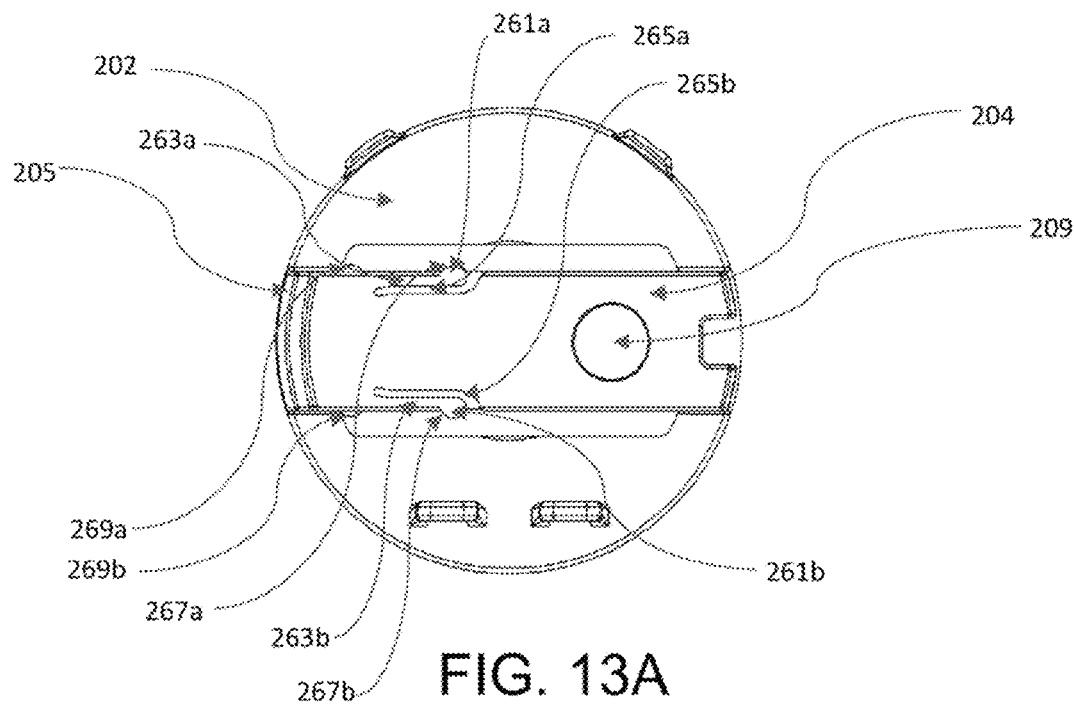
FIG. 13A is a front view of some of the components in a closed configuration of the embodiment of the valve appliance shown in FIG. 11A.
Figure 13B:
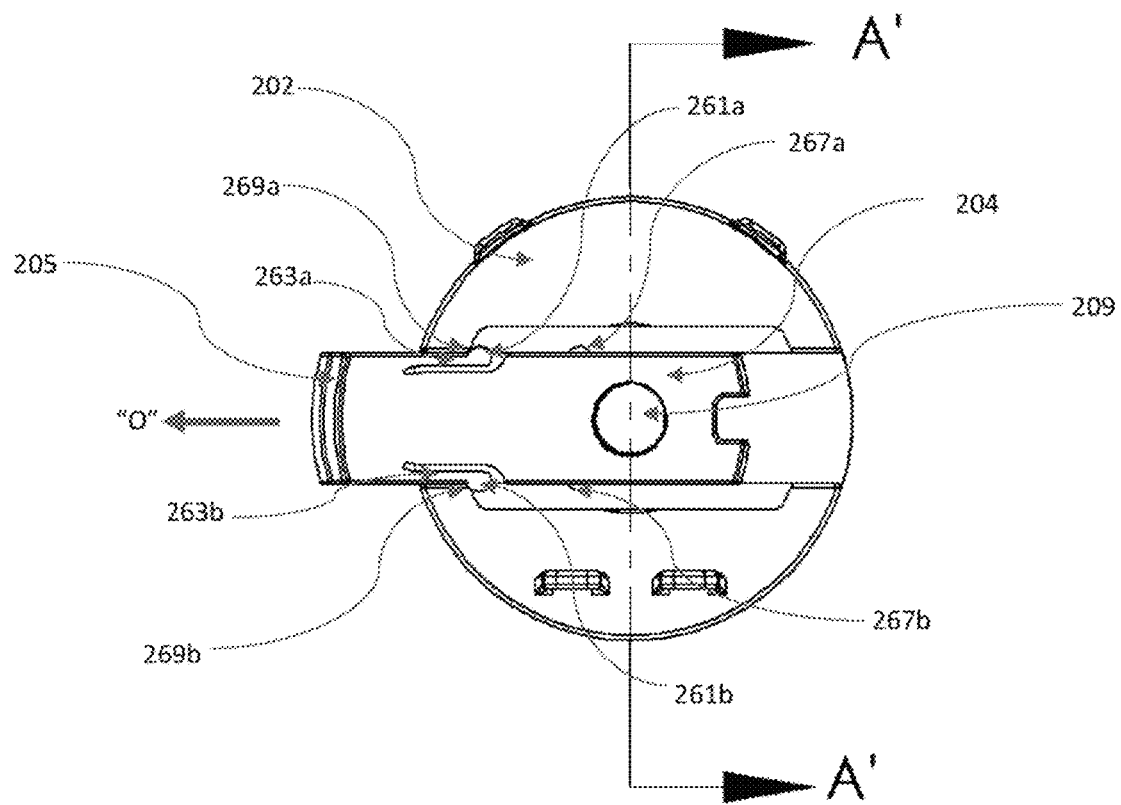
FIG. 13B is a front view of some of the components in an open configuration of the embodiment of the valve appliance shown in FIG. 11A.
Figure 14:
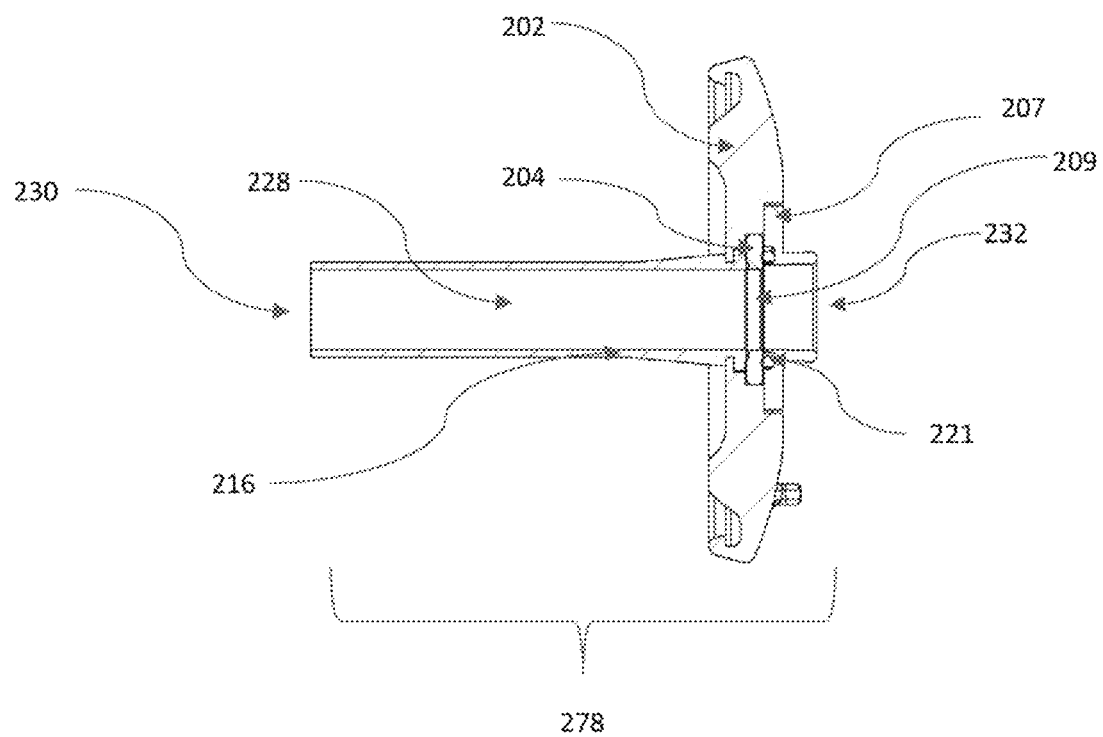
FIG. 14 is a cross-sectional view of some of the components of the embodiment of the valve appliance of FIG. 11A in the open configuration of FIG. 13B through line A'-A'.

The valve cover 207 and nozzle cap 208 have been removed from FIGS. 13A and 13B to facilitate the description of the operation of opening and closing the valve appliance 200. In FIG. 13A, the gate valve 204 is in the closed position and is substantially aligned with the base 202. The gate valve is shown with cantilevered arms 263a and 263b that are formed by arm slots 265a and 265b. The ends of the cantilever arms 263a and 263b have detents 261a and 261b. The detents 261a and 261b are constrained in closed pockets 267a and 267b formed in the base 202. The detents 261a and 261b, and closed pockets 267a and 267b are configured to constrain the gate valve 204 relative to the base 202 and prevent the gate valve 204 from sliding unintentionally thereby keeping the valve appliance 200 closed. When the patient wants to open the valve appliance 200, they pull the valve handle 205 in the direction shown by arrow "O" in FIG. 13B. When the pulling force of the detents 261a and 261b against the closed pockets 267a and 267b is sufficient, the cantilever arms 263a and 263b will flex into the arm slots 255a and 265b and the detents 261a and 261b will release from the closed pockets 267a and 267b. The gate valve 204 will then slide until the detents 261a and 261b engage with the open pockets 269a and 269b that are formed in the base 202. The cantilever arms 263a and 263b will then spring back to hold the detents 261a and 261b in the open pockets 269a and 269b. In this open configuration the gate valve 204 gate opening 209 is aligned with the entry port 230, drain passage 228, base opening 231 and valve cover opening 232 such that there is a complete valve passage 278 as seen in FIG. 14. The valve appliance 200 is open in this configuration and effluent can exit the patient's body. When the patient is finished removing effluent, they apply a force to the valve handle 205 in the direction opposite arrow "O" and slide the gate valve 204 back to the closed position. In this manner the patient controls the timing of effluent exiting their body.

Figure 15A:
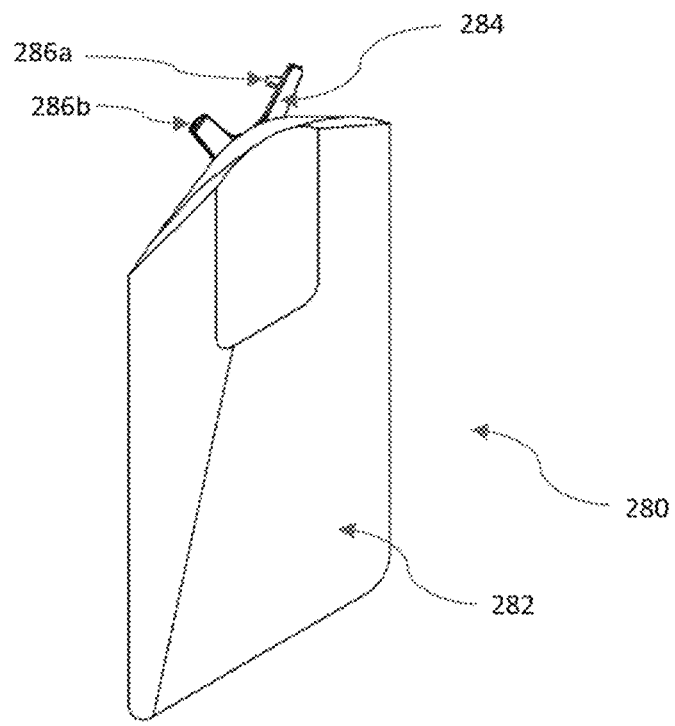
FIG. 15A is a front perspective view of an effluent capture device to be used with the embodiment of the valve appliance shown in FIG. 11A.
Figure 15B:
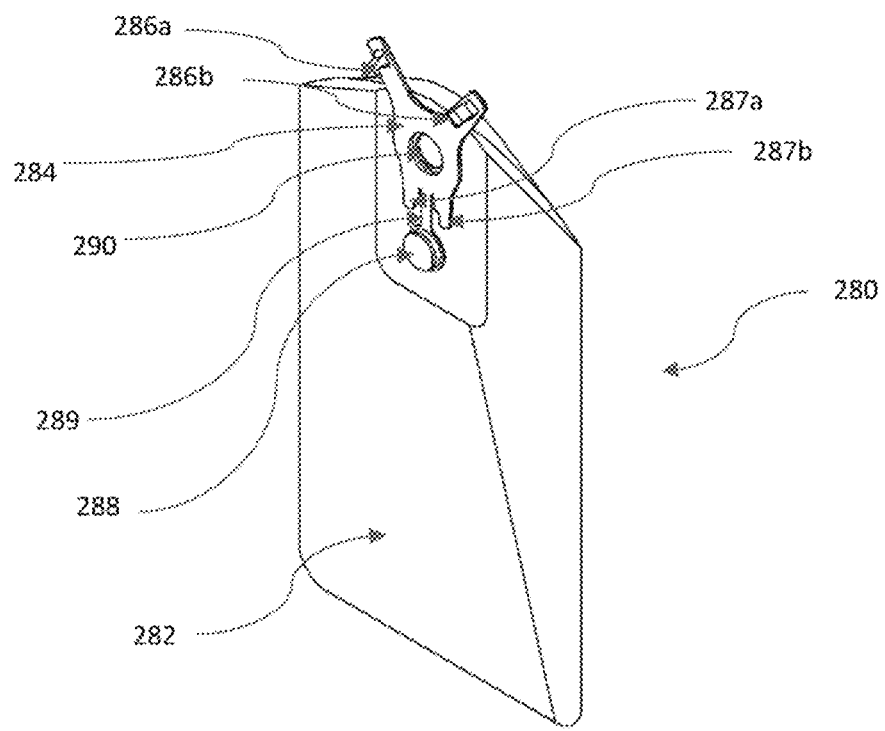
FIG. 15B is a rear perspective view of an effluent capture device shown in FIG. 15A.

When the effluent exits the valve cover opening 232, it is preferred that the effluent be collected in a waste bag 280 such as shown in FIGS. 15A and 15B, for example. The waste bag 280 is comprised of a pouch 282 to hold the waste and a clip 284 to connect the waste bag 280 to a valve appliance such as valve appliance 200. The clip 284 is comprised of one or more hooks 286a and 286b and one or more tabs 287a and 287b that are configured to hold the waste bag 280 to the valve appliance 200. The clip 284 also contains an opening 290 that is configured to engage with the exit nozzle 226 to ensure that effluent coming out of the exit nozzle 226 goes into the pouch 282 and does not leak or spill. The clip can also include a bag cap (plug) 288 that is connected to the clip by a flexible tether 289. The bag cap 288 can be used to seal the opening 290 after the waste bag 280 has collected effluent from the valve appliance 200 and the waste bag 280 is separated from the valve appliance 200. The opening 290 can be configured with a seal to seal against the exit nozzle 226 or against the bag cap 288 to ensure effluent doesn't leak at this connection.

Figure 16:
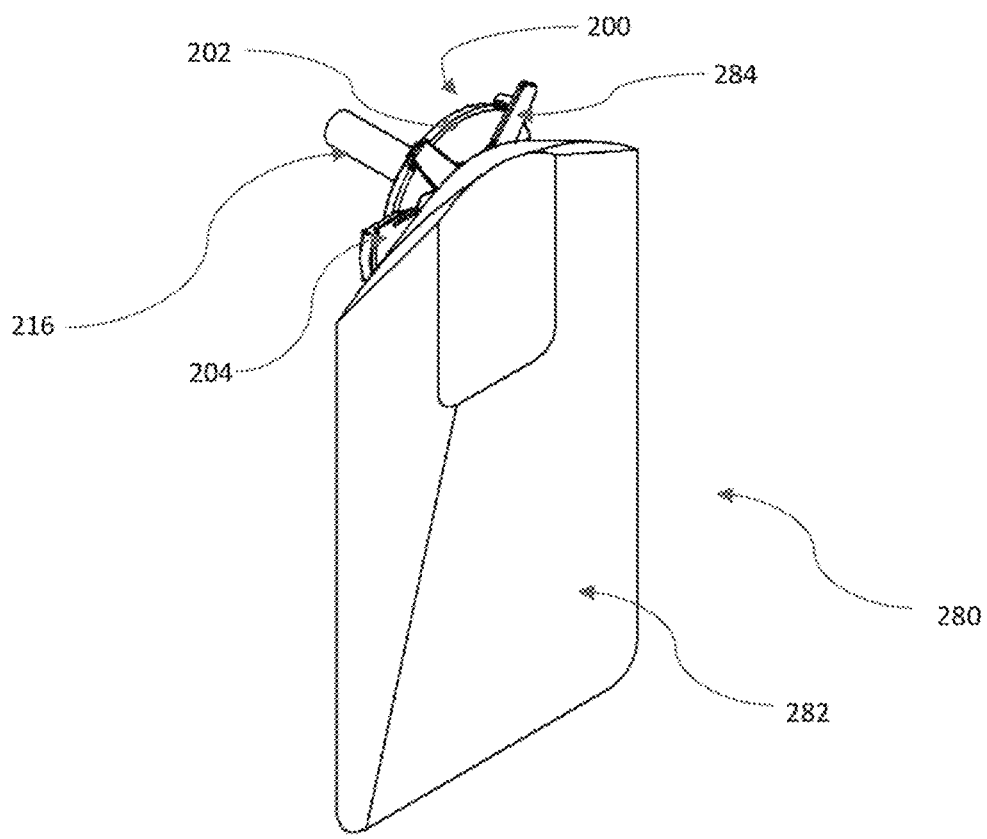
FIG. 16 is a perspective view of an effluent capture device shown in FIG. 15A combined with the embodiment of the valve appliance shown in FIG. 11A.
Figure 17:
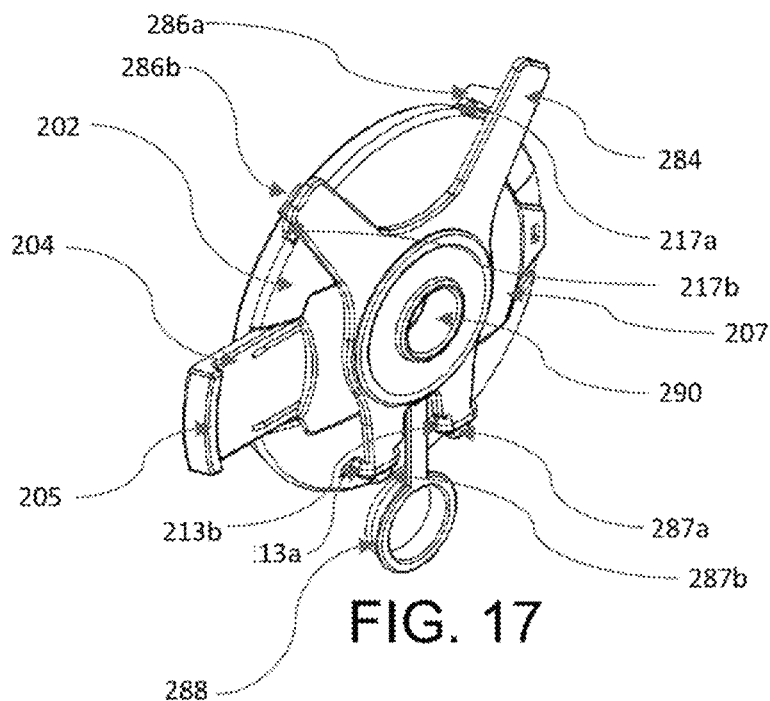
FIG. 17 is a perspective view of some of the components of an effluent capture device shown in FIG. 15A combined with some of the components of the embodiment of the valve appliance shown in FIG. 11A.

FIG. 16 shows the waste bag 280 attached to the valve appliance 200 with the valve appliance 200 in an open configuration to empty effluent from the patient through the valve appliance 200 and into the waste bag 280. In FIG. 17 the pouch 282 has been removed from the clip 284 to show details of how the waste bag 280 is connected to the valve appliance 200. The one or more tabs 287a and 287b of the clip 284 are inserted into the one or more bag clip engagement slots 213a and 213b on the base 202 and the one or more hooks 286a and 286b of the clip 284 are snapped over the one or more bag clip engagement tabs 217a and 217b. This secures the clip 284 and therefore the waste bag 280 to the valve appliance 200 and engages the waste bag 280 opening 290 with the exit nozzle 226. In use, the patient will first attach the waste bag 280 to the valve appliance 200 before opening the gate valve 204 by pulling on the valve handle 205. Then the effluent will flow through the open valve appliance 200 and into the waste bag 280. After all effluent has been removed through the patient's stoma, the patient will then push the valve handle 205 to close the gate valve 204. After the valve appliance 200 is closed, the patient will disengage the clip 284 and remove the waste bag 280 from the valve appliance 200. Then the bag cap 288 can be placed on the opening 290 of the waste bag to prevent effluent from leaking. The nozzle cap 208 can also be placed over the exit nozzle 226 of the valve appliance 200.

The base 202, gate valve 204, valve cover 207, and bag clip 284 can all be fabricated from a rigid plastic resin such as, but not limited to, polypropylene, ABS, polycarbonate, and any blend of such materials. These parts also could be manufactured from metals like aluminum or stainless steel. The substrate portion of adhesive wafer 206 can be fabricated from a flexible material such as, but not limited to, silicone, polyurethane foam or film, TPE (thermoplastic elastomer), polyethylene foam or film, PVC foam, nitrile rubber, and any blend of such materials. The adhesive portion of adhesive wafer 206 can be fabricated from either acrylic or synthetic rubber hydrocolloid adhesive or other adhesives that are skin compatible. The stem 216 can be fabricated from a flexible material such as, but not limited to, silicone, polyurethane, TPU, TPE, polyethylene. The stem 216 can be fabricated from rigid or semi-rigid plastic resins such as but not limited to polypropylene, abs, polycarbonate, and any blend of such materials. The gas-permeable filter 238 can be fabricated from materials such as but not limited to such as polyester, rayon, acrylic, polyethylene, polypropylene, cotton, and blends of such. These materials can natural hydrophobic properties or they can be treated with coatings such as but not limited to bifunctional polysiloxanes to achieve hydrophobic performance. The annular seal 216 can be fabricated from a flexible or semi-rigid material such as put not limited to silicone, polyurethane, TPU, TPE, and other elastic materials. The waste bag 280 can be fabricated from a flexible material such as but not limited to polyethylene, LDPE, HDPE, and other resin films.

In a further alternative embodiment, instead of pouch 282, clip 284 as described above may be provided on a flexible discharge tube to allow the patient to direct waste directly into a toilet. In another alternative, a flexible discharge tube may be provided with an outside diameter at one end that is sized for a slight interference fit with the inside diameter of exit nozzle 226, whereby the discharge tube may be securely inserted into the exit nozzle 226 when needed. Alternately, the inside diameter at one end of the discharge tube is sized for a slight interference fit with the outside diameter of the exit nozzle 226 to secure the discharge tube to the exit nozzle 226 to direct waste into a toilet. A flexible discharge tube of this type may be more conveniently carried by a patient in situations where the patient has access to appropriate waste disposal facilities.

Figure 18A:
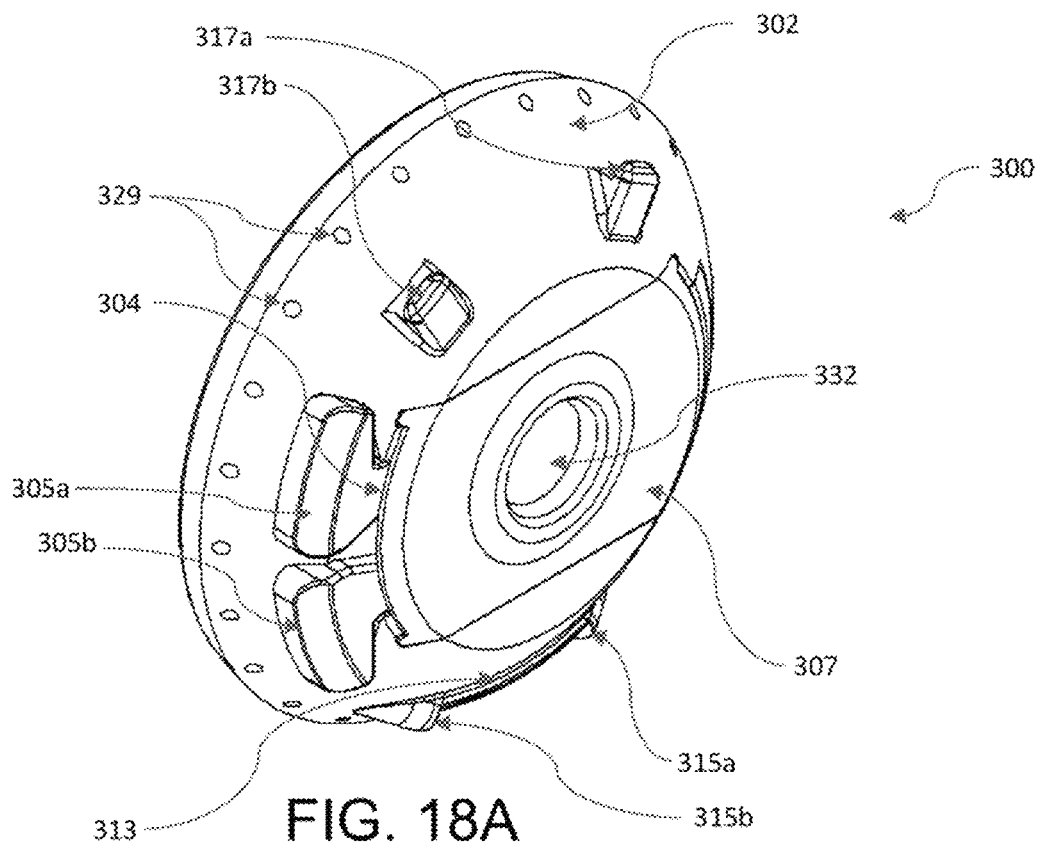
FIG. 18A is a perspective view of another embodiment of a valve appliance.
Figure 18B:
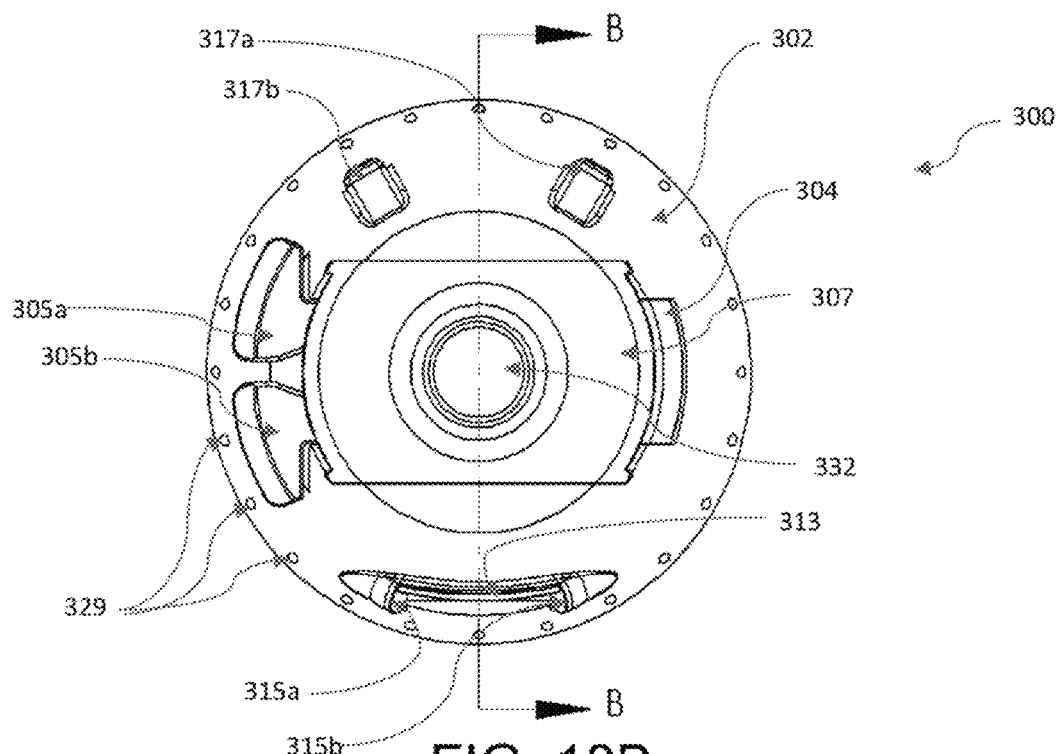
FIG. 18B is a front view of the embodiment of the valve appliance shown in FIG. 18A.
Figure 18C:
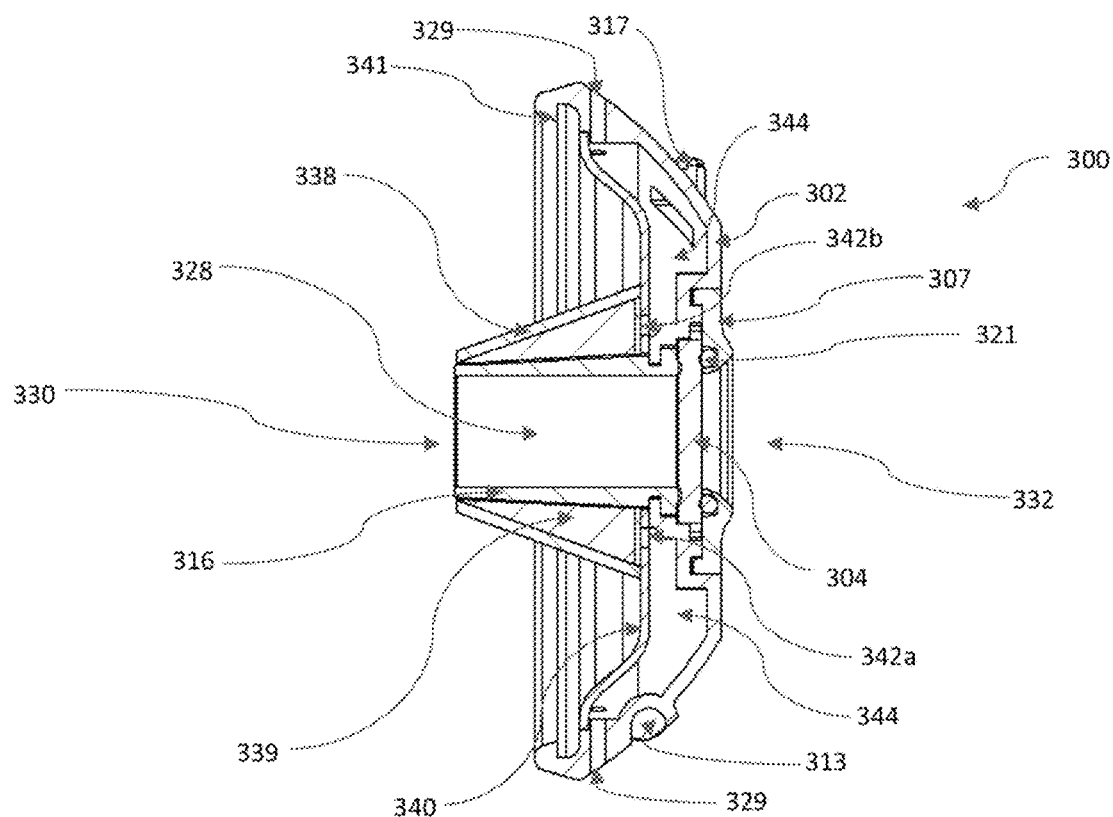
FIG. 18C is a cross-sectional view of the embodiment of the valve appliance shown in FIG. 18B through line B-B.

The description of the valve appliance 200 above is not intended to encompass all possible variations of valve appliances 200 covered by this disclosure. Turning now to FIGS. 18A, 18B and 18C, an alternative embodiment of a valve appliance 300 is shown. This valve appliance 300 is comprised of a base 302, a valve gate 304, a valve cover 307, a seal 321, a stem 316, and a filtration plate 340. The base 302 includes one or more bag clip engagement tabs 317a and 317b, one or more bag clip pockets 313, and one or more bag clip guides 315a and 315b to engage a waste bag clip 384 as will be described further herein. The base 302 is also includes a plurality of vents 329 to vent gases through the valve appliance 300 as will be described further herein. The valve cover 307 includes an exit port 332 to allow effluent to leave the valve appliance 300. The seal 321 is located between the gate valve 304 and the valve cover 307 to ensure that effluent does not leak between the gate valve 304 and the valve cover 307 (see FIG. 18C). The stem 316 has an entry port 330 to allow effluent to enter the drain passage 328 that passes through the center of the stem 316. The stem 316 can also seal against the gate valve 304 to ensure that effluent does not leak between the stem 316 and the gate valve 304.

The stem 316 is surrounded by a primary gas permeable filter 338 that is configured to be compressed against the inside diameter of the stoma and prevent effluent from leaking between the outer surface of the primary gas permeable filter 338 and the stoma. The stem 316 can also be surrounded by a secondary gas permeable filter 339 that is sandwiched between the stem 316 and the primary gas permeable filter 338. The secondary gas permeable filter 339 can be configured with finer filtration than the primary gas permeable filter 338. Providing more than one permeable filter can enable the valve appliance 300 to block solid material and more viscous liquid material with the primary gas permeable filter 338 and block all remaining liquid with the secondary gas permeable filter 339 while allowing gas to pass through. The valve appliance 300 is not limited to just two layers of filters. Any number of filter layers of varying filtration capabilities are possible. Having multiple layers of filtration capabilities allows liquid and solid material to be blocked and gas to pass through without the liquid and solid material clogging the first layer of filter.

It is important for the valve appliance 300 to allow the passage of gas so that the gas does not build up in the patient's digestive tract and cause uncomfortable pressure and sensations. The ability for the valve appliance 300 to release gas continuously while holding liquids and solids until the patient chooses to remove that effluent helps reduce the frequency the patient operates the valve appliance to remove effluent. Gas that passes through the primary gas permeable filter 338 and the secondary gas permeable filter 339 is directed through one or more entry ports 342a-b in the filtration plate 340. The filtration plate 340 is secured to the back side of the base 302 to form a filtration cavity 344 between the base 302 and the filtration plate 340. The filtration plate 340 can be secured to the base 302 with adhesive bonding or any other type of bonding such as ultrasonic welding. The filtration cavity 344 can be filled with an odor absorbing material including but not limited to activated charcoal. The activated charcoal will absorb odors from gases passing through the filtration cavity before the gasses exit the valve appliance 300 through the plurality of exit ports 329. In this manner the valve appliance 300 can continuously release filter gases that do not have an unpleasant odor while allowing the patient to choose when to open and close the valve appliance 300 to remove liquid and solid effluent.

Figure 18D:
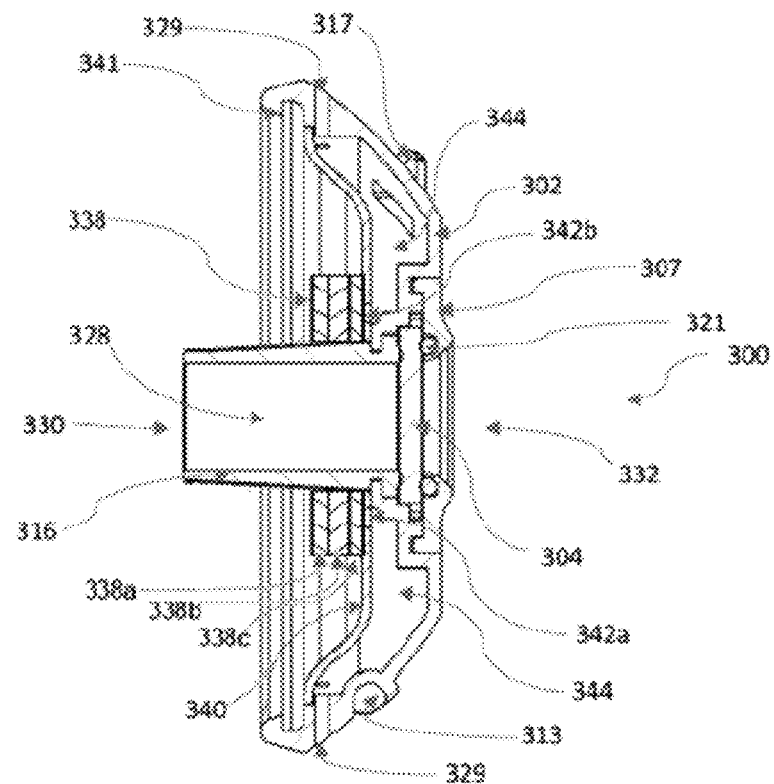
FIG. 18D is a cross-sectional view of the valve appliance as shown in FIGS. 18A and 18B with an alternative filter-seal arrangement.

In addition to providing a seal between the stem 316 and the patient's stoma and a filter for gases, the gas permeable filter 338 also provides a soft interface between the stoma and the valve appliance 300. A soft interface is important to ensure that the valve appliance 300 that can be worn in place for several days before removal and replacement does not irritate the stoma. In addition to covering the stem 316, the secondary gas permeable filter 339, and the one or more entry ports 342a-b, the gas permeable filter 338 can also cover the outer surface of the filtration plate 340. In this manner the gas permeable filter 338 can provide a soft interface between all the surfaces of the valve appliance 300 that are in contact with the patient's stoma. An alternate soft material such as gauze dressing typically used on a wound could also be used to cover the outer surface of the filtration plate 340 instead of the gas permeable filter 338 to provide a soft interface between the valve appliance 300 and the patient's stoma. In a further alternative embodiment, illustrated in FIG. 18D, primary gas permeable filter/seal 338 is configured as an annular disk filter/seal fitted around stem 316. When configured as an annular disk filter/seal, primary filter/seal 338 may be a multi-layer structure wherein each layer is designed to filter a specific particle size. For example, a first inner layer 338a may have a filter pore size in the range of about 0.2-1.0 millimeters (example materials include—polyurethane foam; metal mesh; vinyl mesh) in order to remove macroscopic solids, a second, intermediate layer 338b may have a filter pore size in the range of about 10-50 microns (example materials include polypropylene or rayon) to capture microscopic solids, and third, outer layer 338c may have a filter pore size in the range of about 0.2-0.5 microns (example materials include PTFE) to prevent liquids from entering entry ports 342a,b. In this manner filter plugging may be reduced, allowing gasses to escape while continuing to seal against liquid escape into filtration cavity 344.

Valve appliance 300 may be attached to the patient using an annular disk attachment member such as adhesive wafer 206 as described above. For this purpose base 302 may be provided with annular base clip 341 configured to engage wafer clip 243, as shown, for example, in FIG. 11C (where wafer clip 243 alternatively engages base clip 241 of base 202). Alternative means of patient attachment as described above also may be used. Base 302 is also preferably formed with an interior domed shape as shown, for example, in FIG. 18C, to accommodate the patient's stoma, which may protrude from the surrounding skin surface.

Figure 18E:
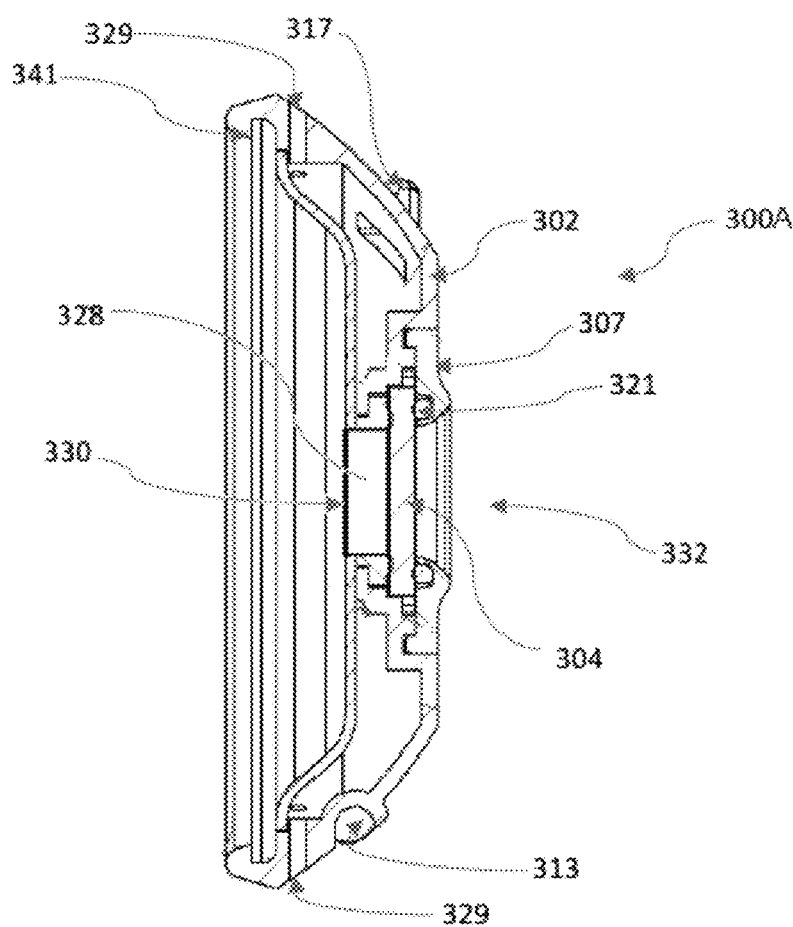
FIG. 18E is a cross-sectional view of an alternative valve appliance similar to the embodiment shown in FIG. 18A, but with no stem or gas vent.
Figure 19A:
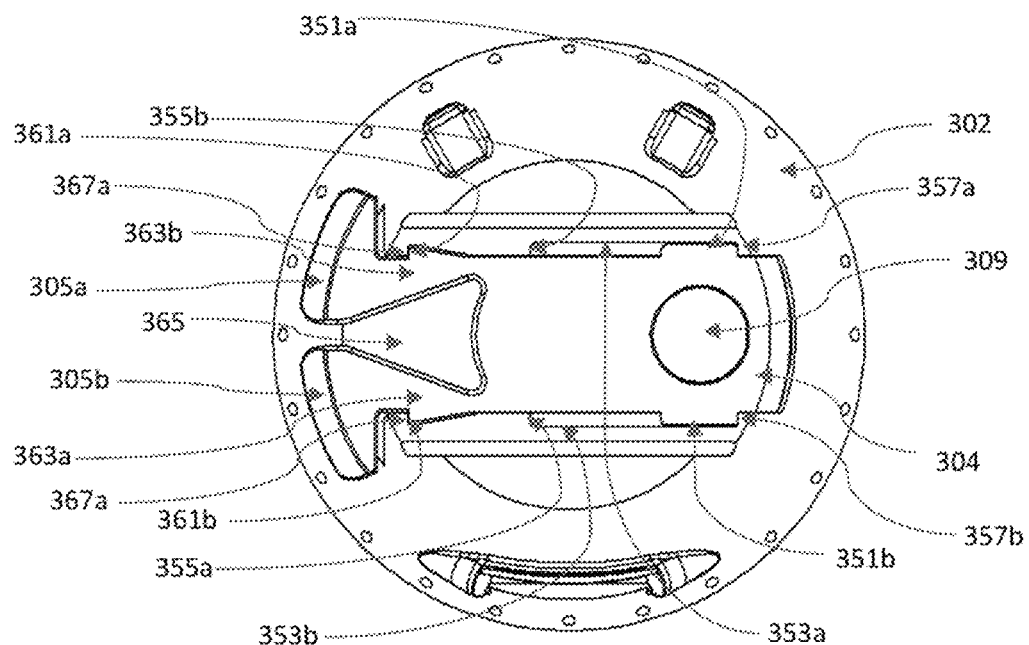
FIG. 19A is a front view of some of the components in a closed configuration of the embodiment of the valve appliance shown in FIG. 18A.
Figure 19B:
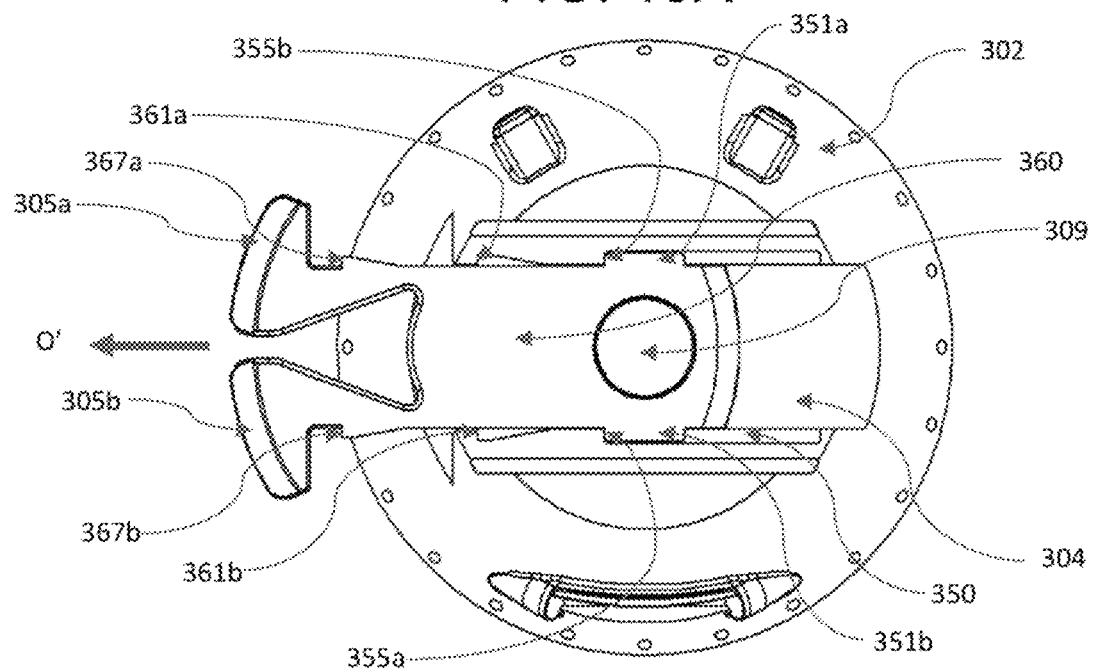
FIG. 19B is a front view of some of the components in an open configuration of the embodiment of the valve appliance shown in FIG. 18A.

The valve cover 307 and seal 321 have been removed from FIGS. 19A and 19B to illustrate the operation of the valve appliance 300. The valve gate 304 is comprised of a body 360, gate guides 351a and 351b on either side of the body 360, cantilever arms 363a and 363b at one end of the body 360, and valve handles 305a and 305b on the ends of the cantilever arms 363a and 363b. The valve gate 304 is held constrained in a closed position relative to the base 302 by lateral stops 361a and 361b that project from the cantilever arms 363a and 363b that butt against stop ledges 367a and 367b on the base 302. To open the gate valve 304, the patient squeezes the valve handles 305a and 305b towards each other and pulls the gate valve 304 in the direction of the "Arrow O'". Squeezing the valve handles 305a and 305b towards each other deflects cantilever arms 363a and 363b which in turn displaces the lateral stops 361a and 361b such that they are free of the stop ledges 367a and 367b. The gate guides 351a and 351b slide against the lateral sides 353a and 353b of the base slot 350 to keep the gate valve moving in the direction of the Arrow O' until the gate guides 351a and 351b butt against the slot ledges 355a and 355b. When the gate guides 351a and 351b butt against the slot ledges 355a and 355b the gate opening 309 through the gate valve 304 is aligned with the drain passage 328 and effluent can exit the patient. The patient can push the valve handles 305a and 305b in the direction opposite Arrow O' to close the gate valve 304. Although the valve appliance 300 illustrated in FIGS. 18A through 19B only has one set of lateral stops 361a and 361b and stop ledges 367a and 367b that hold the gate valve 304 locked until the patient wants to open the valve appliance 300 to remove effluent, the valve appliance 300 could also be comprised of another set of stops and ledges to hold the gate valve 304 open until the patient wanted to close the valve appliance 300. For example, the closed pockets 267a-b and the open pockets 269a-b engaging the detents 261a-b in valve appliance 200 illustrate locking the gate valve 200 in both closed and open positions.

In a further alternative, as illustrated in FIG. 18E, valve appliances according to the present disclosure may be configured without a stem or gas vent. As one such example, alternative valve appliance 300A is structured substantially the same as valve appliance 300, but without stem 316 and without the ports, filters and passages associated with the gas vent.

Figure 20A:
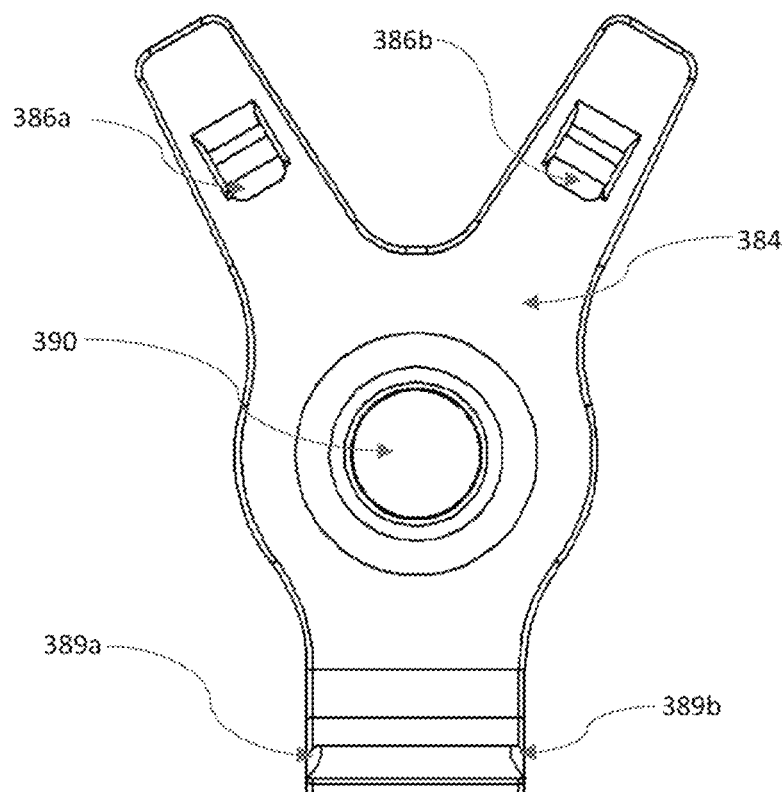
FIG. 20A is a rear view of the alternate effluent capture device clip.
Figure 20B:
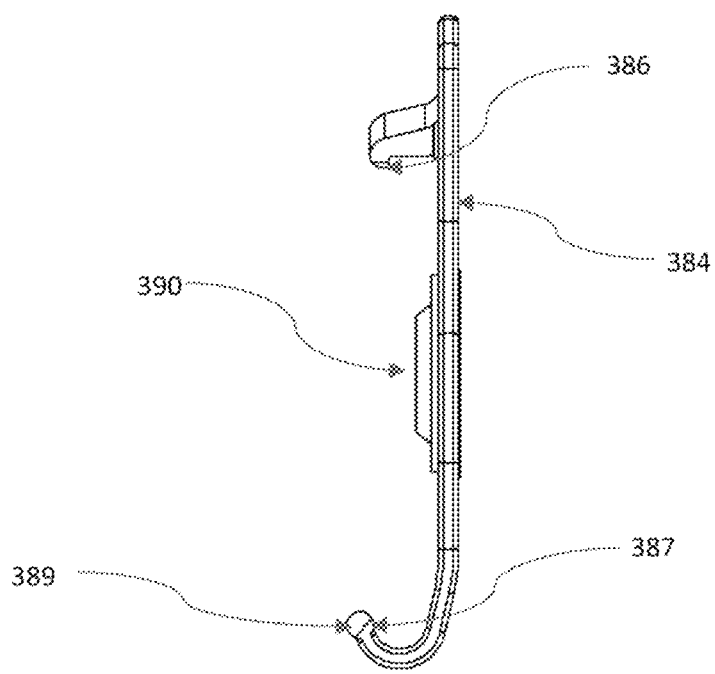
FIG. 20B is a side view of the alternate effluent capture device clip shown in FIG. 20A.
Figure 21:
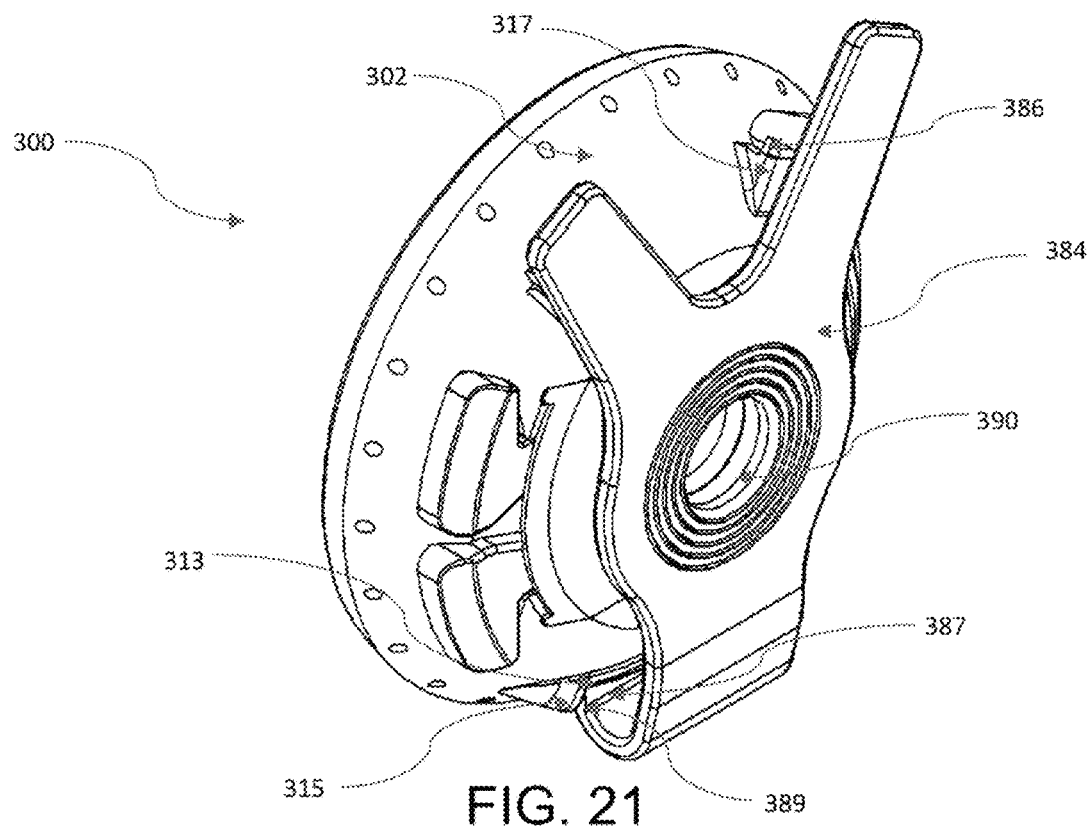
FIG. 21 is a perspective view of the valve appliance shown in FIG. 18A combined with the alternate effluent capture device clip shown in FIGS. 20A-B.

FIGS. 20A and 20B illustrate an alternative embodiment of a waste bag clip 384 with the pouch 282 that would be connected to the waste bag clip 384 not shown so as to highlight the features of the waste bag clip 384. The waste bag clip 384 is comprised of one or more hooks 386a and 386b and one or more tabs 387 that are configured to hold the waste bag clip 384 to the valve appliance 300. The waste bag clip 384 also has an opening 390 that is configured to engage with the exit port 332 of the valve appliance 300 to ensure that effluent coming out of the exit port 332 goes into the pouch 282 and does not leak or spill. The one or more tabs 387 have one or more guiding surfaces 389a and 389b configured to align the one or more tabs 387 with the clip pocket 313 on the valve appliance 300 base 302 (See FIGS. 18A-C and 21). To attach the waste bag clip 384 to the base 302, the one or more tabs 387 of the waste bag clip 384 is placed into the clip pocket 313 on the base 302. The guiding surfaces 389a and 389b on the one or more tabs 387 interface with the sides 315a and 315b of the clip pocket 313 to facilitate the placement of the one or more tabs 387 into the clip pocket 313. The waste bag clip 384 is then pushed against the base 302 until the one or more hooks 386a and 386b of the waste bag clip 384 catch the one or more bag clip engagement tabs 317a and 317b on the base 302. Once the waste bag clip 384 and with it the waste bag 28 is securely attached to the valve appliance 300, the patient can open the valve gate 304 to remove effluent from their body. The valve appliance 300 or 200 can be used without a waste bag clip to remove effluent from the body into a toilet of similar receptacle but use of the waste bag 280 can make the process easier and cleaner for the patient.

The base 302, gate valve 304, valve cover 307, and bag clip 384, and filtration plate 340 can all be fabricated from similar materials as were described herein for the base 202, gate valve 204, valve cover 207, and bag clip 284 Similarly, the stem 316 can be fabricated from similar materials as were described herein for the stem 216. It is also to be noted that while stem 316 is shown in this example to be shorter than the stems of other embodiments, for example stem 216, stems of varying lengths or no stem may be utilized with any of the disclosed embodiments. Where a stem is included, it may vary in length from having an inner end lying approximately co-planar with the inside surface of the base to the longer stems shown in various embodiments. One factor bearing on stem length would be patient comfort. Specific vent designs also may require longer or shorter stems.

FIGS. 22A-E illustrate another alternate embodiment of a valve appliance 400. The valve appliance 400 is comprised of a base 402, an adhesive wafer 406, a ball valve 434, a valve lock 401, and a stem 416. The base 402 is configured on the front side with a ball cavity 420 and a tube cavity 422. The ball cavity 420 is configured with two side slots 433a-b. The ball cavity is configured to accept the ball valve 434 and the side slots 433a-b are configured to accept the ball axels 435a-b. The ball valve 434 pivots relative to the base 402 around the axis formed by the ball axels 435a-b. The base is also comprised of one or more filter cavities 453a-b. The one or more filter cavities 453a-b are covered with one or more filter cavity covers 452a-b. The one or more filter cavity covers 452a-b contain order absorbing material inside the one or more filter cavities 453a-b. The one or more filter cavity covers 452a-b can be attached to the base 402 with adhesive bonding or any other type of bonding including ultrasonic welding, solvent bonding, insert molding, and the like. The one or more filter cavity covers 452a-b contain a plurality of openings 454 to allow gases to pass through the odor absorbing material in the one or more filter cavities 453a-b and out of the valve appliance 400. The base 402 is configured on the back side with one or more ribs 494 that interface with one or more grooves 492 on the adhesive wafer to securely attach the base 402 to the adhesive wafer 406. The ribs 494 and grooves 492 can be attached with adhesive bonding or any other type of bonding including ultrasonic welding, solvent bonding, insert molding, and the like.

The adhesive wafer 406 is comprised of one or more grooves 427. The one or more grooves 427 can be on either the front surface or the back surface of the adhesive wafer 406 and provide for a more flexible adhesive wafer 406 to optimize the adhesive wafer's 406 conformation and adherence to the patient's skin. The back side of the adhesive wafer 405 is comprised of a skin compatible adhesive to ensure the valve appliance 400 can be adhered to the patient's skin for several days to keep the valve appliance 400 in position without irritating the patient's skin.

The ball valve 434 is also comprised of an exit nozzle 404 at the end of which is the exit port 415. The ball valve 434 also has a bottom port 418 which is in communication with the exit port 516 by means of a nozzle passage 417 (See FIG. 23C).

The valve lock 401 is comprised of an elongated rod 403 with an end face 413 at one end and a lock handle 405 at the other end. The valve lock 401 also has a wiping edge 425 adjacent to the end face 413. The elongated rod 403 fits in the nozzle passage 417 of the ball valve 434 with the wiping edge 425 extending past the exit nozzle 404. The outer diameter of the wiping edge 425 is greater than the inside diameter of the nozzle passage 417 and thereby holds the valve lock 401 inside the ball valve 434 with the valve lock 401 preventing the ball valve 434 from rotating thereby locking the ball valve 434 and keeping the valve appliance 400 closed. The valve lock 401 also has a guide channel 410 with a guide stop 414 near the end face 413. The guide channel is configured to slide over a stop boss 412 on the base 402. When the valve lock 401 is actuated as will be described further herein, the stop boss 412 prevents the valve lock 401 from rotating, and the guide stop 414 prevents the valve lock 401 from being separated from the valve appliance 400.

The stem 416 is attached to the base 402 and is covered by a gas permeable filter 438. The back end of the stem 416 has an entry port 430 that allows effluent to enter the drain passage 428. The front end of the stem 416 is compressed against the ball valve 434 to prevent effluent from leaking from the stem when the valve appliance 400 is in the locked position. The gas permeable filter 438 is comprised of one or more wicks 439 that pass-through slots 440 in the base 402 to the one or more filter cavities 453a-b.

Figure 23A:
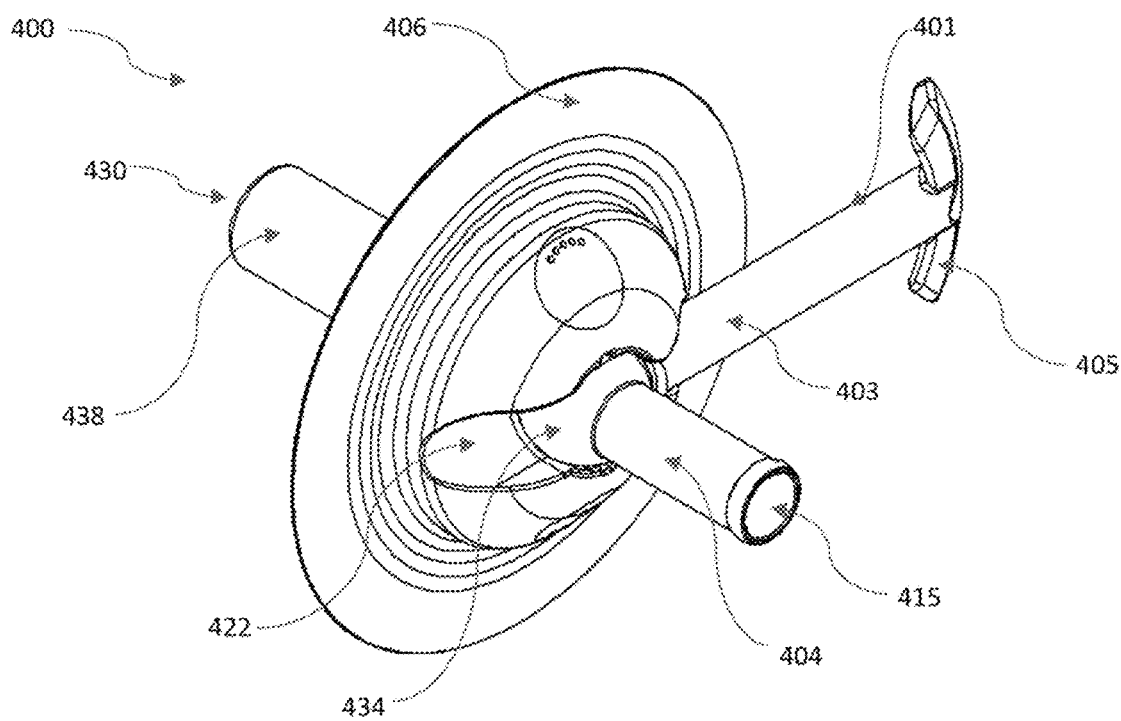
FIG. 23A is a perspective view of the embodiment of the valve appliance shown in FIG. 22A in an open configuration.
Figure 23B:
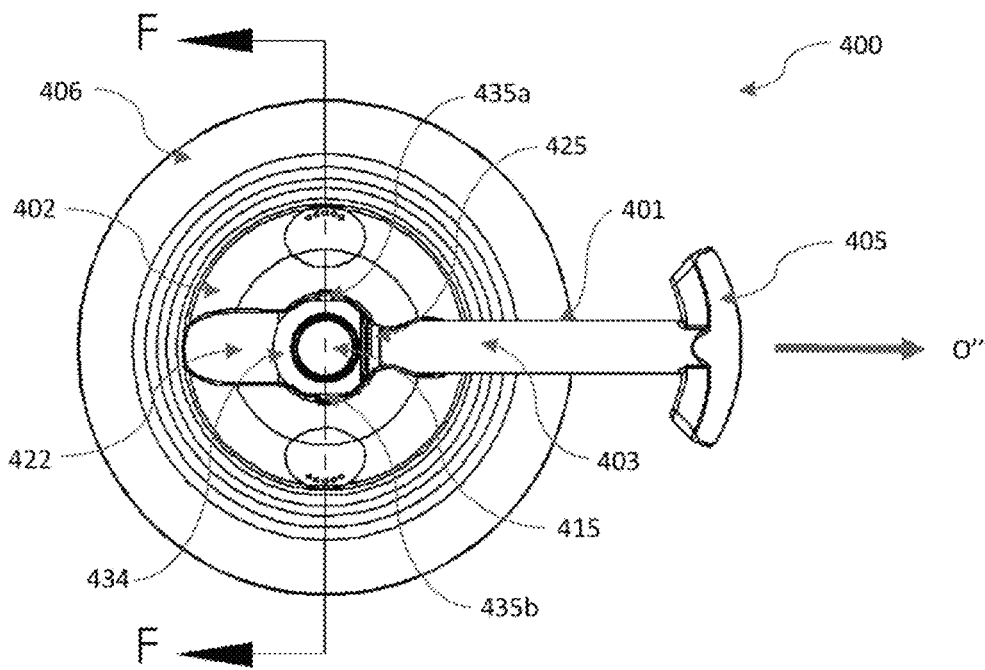
FIG. 23B is a front view of the embodiment of the valve appliance shown in FIG. 23A.
Figure 23C:
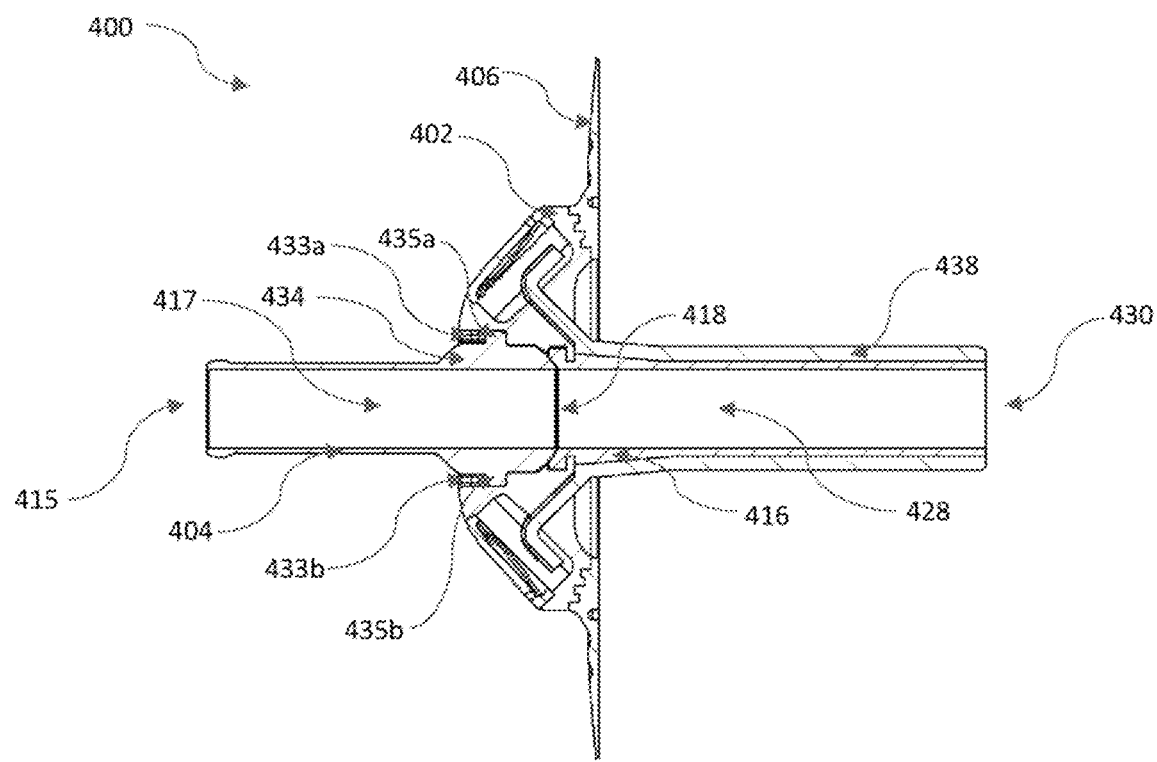
FIG. 23C is a cross-sectional view of the embodiment of the valve appliance shown in FIG. 23B through line F-F.

FIGS. 23A, 23B and 23C show the valve appliance 400 in an open position. To open the valve appliance 400, the patient first holds the lock handle 405 and slides the valve lock 401 in the direction of Arrow O". This action pulls the wiper edge 425 into the exit port 415 and through the nozzle passage 417 of the ball valve 434. When the valve lock 401 is completely withdrawn from the ball valve 434, the guide stop 414 contacts the stop boss 412 of the base 402 preventing additional translation of the valve lock 401. The patient then holds the exit nozzle 404 of the ball valve 434 and pivots the ball valve 434 about the axis formed by the ball axels 435a-b. This moves the ball valve 434 from the horizontal locked position to a vertical open position. In this open position, there is a continuous opening created starting from the entry port 430 on the end of the stem 416, through the drain passage 428 in the stem 416, to the bottom port 418 on the ball valve 434, through the nozzle passage 417 in the exit nozzle 404, and ending at the exit port 415. In this manner effluent can enter the valve appliance 400 through the entry port 430 and leave through the exit port 415 and the patient can remove effluent from their body.

After removing all effluent, the patient can rotate the ball valve 434 back to a horizontal position closing the valve appliance 400. Then the patient can slide the valve lock 401 back into the ball valve 434. The wiper edge 425 is pushed into the bottom port 418, through the nozzle passage 417 in the exit nozzle 404, and out the exit port 415. This actuation of the valve lock 401 with the wiper edge 425 near the end face 413 cleans out any effluent that may be still present in the nozzle passage 417 so that the ball valve 434 is clean until the next time the patient wants to actuate and open the valve appliance 400.

The base 402, ball valve 404, cavity covers 452a-b, and valve lock 401, can all be fabricated from similar materials as were described herein for the base 202, gate valve 204, and valve cover 207. Similarly, the wafer 406, the stem 416, gas permeable filter 438, and wiping edge 425 can be fabricated from similar materials as were described herein for the wafer 206 and the stem 216, gas permeable filter 238, and annular seal 221, respectively.

In further alternative embodiments, valve appliances may be configured substantially as described hereinabove, but without a gas vent. The need for gas venting in some cases may be correlated to patient personal habits such as frequency of evacuation and diet. Patients that do not require a gas vent may therefore prefer the greater control that could be afforded by a ventless valve appliance. Further, in some embodiments it may be preferable to not include the stem component while otherwise configuring valve appliance embodiments in accordance with the embodiments described herein. Removal of the stem component for some patients may increase comfort of the device. Additionally, as one purpose of the stem in some embodiments is to create functionally separate pathways for evacuation of gas versus liquid/solid wastes, it may be desirable to omit the stem component in unvented embodiments.

In view of the foregoing, the improvements discussed herein can facilitate discharge of waste from stoma. The embodiments employ materials that self-seal with surfaces inside of the patient's body. This feature eliminates the need for the patient to interact with the device to properly affix it in position so as to avoid leaks or other potential mistakes that can allow waste to inadvertently discharge from the stoma.

The foregoing has been a detailed description of illustrative embodiments of the disclosure. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this disclosure. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present disclosure. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this disclosure.

Exemplary embodiments have been disclosed above and illustrated in the accompanying drawings. It will be understood by those skilled in the art that various changes, omissions and additions may be made to that which is specifically disclosed herein without departing from the spirit and scope of the present disclosure.

What is claimed is:

1. A stoma valve appliance, comprising:
   a support member configured to surround a patient stoma and having an inner, skin-facing side and an outer side;
   a base member removably attachable over the support member, said base member defining a first solids and liquids flow path and a second gas vent flow path through the base member, each said flow path having at least one opening on an inner side of the base member;
   a valve disposed in the base member configured to control flow through said first flow path, the valve having an open position permitting flow and a closed position preventing flow and being manipulable between the open and closed position by the patient;

a stem with an inlet and an outlet projecting inwardly from the body member configured to be received in the patient stoma, the stem having sufficient length to extend through the support member to position the inlet in the stoma when the base member is mounted on the support member with the outlet at an opposite end communicating with the first flow path opening in the base member; and a gas permeable filter seal comprising plural filter layers with different pore sizes around the stem covering the at least one second gas vent flow path opening, whereby gasses from the stoma may be vented through said second flow path, while liquids and solids are prevented from entering said second flow path.

2. The stoma valve appliance of claim 1, further comprising means for affixing the support member to the patient's skin disposed on said support member inner, skin-facing side.

3. The stoma valve appliance of claim 2, wherein the means for affixing comprises an adhesive material.

4. The stoma valve appliance of claim 1, wherein the gas permeable filter seal comprises a sleeve surrounding at least a portion of the stem configured to extend into the stoma between the stem and the patient.

5. The stoma valve appliance of claim 1, wherein the gas permeable filter seal comprises a disk filter member around the stem and through which the stem extends.

6. The stoma valve appliance of claim 1, wherein the base member gas vent flow path terminates in at least one exhaust port opposite the inner side of the base member and the base member defines at least one filtration cavity in the gas vent flow path between the at least one inner side opening and at least one exhaust port.

7. The stoma valve appliance of claim 6, wherein the at least one filtration cavity contains an odor-absorbing material.

8. The stoma valve appliance of claim 1, wherein the support member and base member are attached by being pressed together and wherein the support member and base member each have facing engagement surfaces that engage and fix said members together when pressed together.

9. The stoma valve appliance of claim 1, wherein the support member and base member are attachable with a threaded connection.

10. The stoma valve appliance of claim 1, further comprising an exit nozzle terminating the first flow path through the base member opposite the inner side opening.

11. The stoma valve appliance of claim 1, wherein the valve is a gate valve.

12. The stoma valve appliance of claim 1, wherein the valve is a ball valve.

13. A stoma valve appliance, comprising:

a support member configured to surround a patient stoma and having an inner, skin-facing side and an outer side;

a base member removably attachable over the support member, said base member defining a first solids and liquids flow path and a second gas vent flow path through the base member, each said flow path having at least one opening on an inner side of the base member, and wherein said second gas vent flow path terminates in at least one exhaust port opposite the inner side of the base member and the base member defines at least one filtration cavity in said gas vent flow path between the at least one inner side opening and at least one exhaust port;

a valve disposed in the base member configured to control flow through said first flow path, the valve having an open position permitting flow and a closed position preventing flow and being manipulable between the open and closed position by the patient;

a stem with an inlet and an outlet projecting inwardly from the body member configured to be received in the patient stoma, the stem having sufficient length to extend through the support member to position the inlet in the stoma when the base member is mounted on the support member with the outlet at an opposite end communicating with the first flow path opening in the base member; and a gas permeable filter seal disposed around the stem covering the at least one second gas vent flow path opening, whereby gasses from the stoma may be vented through said second flow path, while liquids and solids are prevented from entering said second flow path.

14. The stoma valve appliance of claim 13, wherein the at least one filtration cavity contains an odor-absorbing material.

15. The stoma valve appliance of claim 1, further comprising an exit nozzle terminating the first solids and liquids flow path through the base member opposite the inner side opening receiving flow through the valve in the open position.

* * * * *